(12) United States Patent
Zhang et al.

(10) Patent No.: US 7,115,793 B2
(45) Date of Patent: Oct. 3, 2006

(54) ISOLATION AND IDENTIFICATION OF TRANSCRIPTION CONTROL ELEMENTS ASSOCIATED WITH MOUSE EOSINOPHIL PEROXIDASE EXPRESSION

(75) Inventors: Hongbing Zhang, Albany, CA (US); Pamela Contag, San Jose, CA (US); Anthony Purchio, Alameda, CA (US); Amy Holt, Oakland, CA (US)

(73) Assignee: Xenogen Corporation, Alameda, CA (US)

( * ) Notice: Subject to any disclaimer, the term of this patent is extended or adjusted under 35 U.S.C. 154(b) by 45 days.

(21) Appl. No.: 10/990,112

(22) Filed: Nov. 16, 2004

(65) Prior Publication Data

US 2005/0138678 A1 Jun. 23, 2005

Related U.S. Application Data

(62) Division of application No. 10/126,912, filed on Apr. 19, 2002, now Pat. No. 6,858,773.

(60) Provisional application No. 60/285,603, filed on Apr. 20, 2001.

(51) Int. Cl.
*G01N 33/00* (2006.01)
*A01K 67/027* (2006.01)
*C07H 21/04* (2006.01)

(52) U.S. Cl. .................... 800/3; 800/18; 536/24.1

(58) Field of Classification Search .................. None
See application file for complete search history.

(56) References Cited

U.S. PATENT DOCUMENTS

| | | |
|---|---|---|
| 4,873,191 A | 10/1989 | Wagner et al. |
| 5,229,285 A | 7/1993 | Kajiyama et al. |
| 5,292,658 A | 3/1994 | Cormier et al. |
| 5,330,906 A | 7/1994 | Kajiyama et al. |
| 5,418,155 A | 5/1995 | Cormier et al. |
| 5,464,764 A | 11/1995 | Capecchi et al. |
| 5,604,123 A | 2/1997 | Kazami et al. |
| 5,618,722 A | 4/1997 | Zenno et al. |
| 5,641,641 A | 6/1997 | Wood |
| 5,650,135 A | 7/1997 | Contag et al. |
| 5,650,289 A | 7/1997 | Wood |
| 5,670,356 A | 9/1997 | Sherf et al. |
| 6,217,847 B1 | 4/2001 | Contag et al. |

FOREIGN PATENT DOCUMENTS

WO WO 00/34304 A1 6/2000
WO WO 01/18195 A2 3/2001

OTHER PUBLICATIONS

Blyth, D.I., et al. (2000) "Airway subepithelial fibrosis in a murine model of atopic asthma: suppression by dexamethasone or anti-interleukin-5 antibody," *Am J Respir Cell Mol Biol* Aug. 23(2):241-6.
Burgess, A. W. et al. (1980) "Preparation and surface labeling of murine eosinophils," *Exp. Hematol.* Jan. 8(1):108-119.
Bruselle, et al. (1995) "Allergen-induced airway inflammation and bronchial responsiveness in wild-type and interleukin-4-deficient mice," *Am. J. Respir. Cell & Mol. Biol.* 12:254-259.
Campbell, H.D., et al. (1988) "Isolation, structure and expression of cDNA and genomic clones for murine eosinophil differentiation factor. Comparison with other eosinophilopoietic lymphokines and identity with interleukin-5," *Eur. J. Biochem.* 174(2):345-352.
Capecchi, M.R. (1980) "High efficiency transformation by direct microinjection of DNA into cultured mammalian cells," *Cell* 22:479-488.
Contag, C. H., et al. (1995) "Photonic detection of bacterial pathogens in living hosts," *Mol Microbiol.* 18:593-603.
Contag, C., et al. (1996) *OSA TOPS on Biomedical Optical Spectroscopy and Diagnostics* 3:220-224.
Contag, C.H., et al. (1997) "Visualizing gene expression in living mammals using a bioluminescent reporter," *Photochem Photobiol.* 66:523-31.
Contag, P.R., et al. (1998) "Bioluminescent indicators in living mammals," *Nature Med.* 4:245-7.
Corry, et al. (1996) "Interleukin 4, but not interleukin 5 or eosinophils, is required in a murine model of acute airway hyper-reactivity," *J. Exp. Med.* 183:109.
Cui, X, et al. (1998) "The attenuative effect of purified protein derivative sensitization on T helper 2 reaction and eosinophil infiltration of the lung in ovalbumin sensitized mice," *Chin Med J* (Engl) Oct. 111(10):940-944.
Das, A.M., et al. (1997) "A novel murine model of allergic inflammation to study the effect of dexamethasone on eosinophil recruitment," *Br J Pharmacol.* May, 121(1):97-104.
de Wet, J.R., et al. (1987) "Firefly luceiferase gene: structure and expression in mammalian cells," *Molec. Cell. Biol.* 7:725-737.
Dohi, M., et al. (1999) "Noninvasive system for evaluating the allergen-specific airway response in a murine model of asthma," *Lab Invest* Dec. 79(12):1559-1571.

(Continued)

*Primary Examiner*—Scott D. Priebe
*Assistant Examiner*—Valarie Bertoglio
(74) *Attorney, Agent, or Firm*—Robins & Pasternak LLP

(57) ABSTRACT

The present invention relates to novel transcription control elements derived from a mouse eosinophil peroxidase gene. Such transcription control elements may comprise isolated polynucleotides, expression cassettes, vectors, recombinant cells, and transgenic animals, as described herein.

6 Claims, 20 Drawing Sheets

OTHER PUBLICATIONS

Ellis, J., et al. (1989) "Gene targeting with retroviral vectors: recombination by gene conversion into regions of nonhomology," *Molec. Cell. Biol.* 9:1621-1627.

Farhood et al (1994) "Cationic liposomes for direct gene transfer in therapy of cancer and other diseases," *Annals NY Acad. Sci.*, 716:23-34.

Fattah, D., et al. (1996) "A rapid activation assay for human eosinophils based on adhesion to immobolized ICAM-1, VCAM-1 and IgG," *Cytokine* Mar. 8(3):248-259.

Fradkov, A.F., et al. (2000) "Novel fluorescent protein from Discosoma coral and its mutants possesses a unique far-red fluorescence," *FEBS Lett.* 479(3):127-130.

Gavett, et al. (1994) "Depletion of murine CD4+ T lymphocytes prevents antigen-induced airway hyperreactivity and pulmonary eosinophilia," *Am. J. Respir. Cell & Mol. Biol.* 10:587-593.

Giphart-Gassler, M., et al. (1989) "Studying DNA mutations in human cells with the use of an integrated HSV thymidine kinase target gene," *Mutat. Res.* 214:223-232.

Graham, F., et al. (1973) "A new technique for the assay of infectivity of human adenovirus 5 DNA," *Virology* 52:456-467.

Gribskov (1986) "Sigma factors from *E. coli*, B. subtilis, phage SP01, and phage T4 are homologous proteins," *Nucl. Acids Res.* 14(6):6745-6763.

Hadjantonakis, A.K., et al. (2001) "The color of mice: in the light of GFP-variant reporters," *Hostochem. Cell Biol.* 115(1):49-58.

Hammelmann, et al. (1996) "Requirement for CD8+ T cells in the development of airway hyperresponsiveness in a marine model of airway sensitization," *J. Exp. Med.* 183:1719.

Hoang, T., et al. (1983) "Separation of hemopoietic cells from adult mouse marrow by use of monoclonal antibodies," *Blood* Mar. 61(3):580-588.

Hunt, T.C., et al. (1993) "Monoclonal antibodies specific for guinea pig eosinophil major protein: their use in an ELISA, immunocytochemistry and flow cytometry," *Clin. Exp. Allergy* May 23(5):425-434.

Hyde et al. (1993) "Correction of the ion transport defect in cystic fibrosis transgenic mice by gene therapy," *Nature*, 362:250-255.

Kajiyama, N., et al. (1991) "Isolation and characterization of mutants of firefly luciferase which produce different colors of light," *Protein Engineering* 4(6):691-693.

Koller, B.H., et al. (1992) "Altering genes in animals by gene targeting," *Annual review of immunology* 10:705-730.

Lewis, J.C., et al. (2000) "Photoproteins as Luminescent Labels in Binding Assays," *Fres. J. Anal. Chem.* 366(6-7):760-768.

Littlefield, J.W. (1964) "Selection of hybrids from matings of fibroblasts in vitro and their presumed recombinants," *Science* 145:709-710.

Liu C., et al. (2000) "Kinetic study of eosinophil apoptosis and its relationship to Th2 cytokines in asthmatic murine model," *Chin Med J* (Engl) Sep.:113(9):783-6.

Majzoub et al. (1996) "Knockout Mice," *New Engl. J. Med.* 334:904-907.

Mannino, R., et al. (1998) "Liposome mediated gene transfer," *BioTechniques*, 6:682-690.

Mansour, S.L. et al. (1988) "Disruption of the proto-oncogene int-2 in mouse embryo-derived stem cells: a general strategy for targeting mutations to non-selectable genes," *Nature* 336:348-352.

Mishra, A., et al. (2001) "An etiological role for aeroallergens and eosinophils in experimental esophagitis," *J. Clin. Invest.* 107:83-90.

Mishra, A. (2002) "IL-5 promotes eosinophil trafficking to the esophagus," *J. Immunol.* Mar. 1, 168(5):2464-2469.

Nagy, Andras, et al., "Manipulating the Mouse Embryo: A Laboratory Manual," ISBN: 0879695749, Publisher: Cold Spring Harbor Laboratory Press, Pub. Date: Dec. 2002, Third Edition (*Front page and Table of Contents only*).

Pinkert, Carl A. "Transgenic Animal Technology: A Laboratory Handbook," by First Edition, Academic Press; ISBN: 0125571658 (*Front page and Table of Contents only*).

Plautz et al. (1994) "Direct gene transfer for the understanding and treatment of human disease," *Annals NY Acad Sci.*, 716:144-153.

Potter, H., et al. (1984) "Enhancer-dependent expression of human kappa immunoglobulin genes introduced into mouse pre-B lymphocytes by electroporation," *Proc. Nat'l. Acad. Sci.* U.S.A. 81:7161-7165.

Prasher, D.C., et al. (1987) "Sequence comparisons of complementary DNAs encoding aequorin isotypes," *Biochem.* 26:1326-1332.

Rassoulzadegan, M., et al. (1982) "High frequency of gene transfer after fusion between bacteria and eukaryotic cells," *Nature*, 295:257-259.

Richa, J. (2001) "Production of Transgenic Mice," *Molecular Biotechnology*, Mar. 2001 vol. 17:261-268.

Rothenberg, M.E., et al. (2001) "Gastrointestinal eosinophils," *Immunol. Rev.* Feb., 179:139-155.

Sambrook, "Molecular Cloning: A Laboratory Manual," Publisher: Cold Spring Harbor Laboratory Press, Pub. Date: 1989, Second Edition, Chapter 16.

Shinagawa, K., et al. (2000) "Rapid isolation of homegeneous murine bronchoalveolar lavage eosinophils by differential lectin affinity interaction and negative selection," *J. Immunol. Methods* Apr. 3 237(1-2):65-72.

Spry, "Eosinophils," Oxford University Press, pp. 205-212 (1988).

Tatsumi, H.N., et al. (1992) "Molecular cloning and expression in *Escherichia coli* of a cDNA clone encoding luciferase of a firefly, *Luciola lateralis,*" *Biochim. Biophys. Acta* 1131:161-165.

Thomas, K. R. et al., "Site-directed mutagenesis by gene targeting in mouse embryo-derived stem cells," *Cell* 51:503-512 (1987).

Tomkinson, A., et al. (2001) "Temporal Association between Airway Hyperresponsiveness and Airway Eosinophilia in Ovalbumin-Sensitized Mice," *Am J Respir Crit Care Med* Mar. 163(3 Pt 1):721-30.

Tomkinson, A., et al. (2001) "A murine IL-4 receptor antagonist that inhibits IL-4- and IL-13-induced responses prevents antigen-induced airway eosinophilia and airway hyperresponsiveness," *J Immunol* May 1 166(9):5792-800.

Trifilieff, A., et al. (2000) "Abrogation of lung inflammation in sensitized Stat6-deficient mice is dependent on the allergen inhalation procedure," *Br J Pharmacol* Aug. 130(7):1581-1588.

Trifilieff, A., et al. (2000) "Time course of inflammatory and remodeling events in a murine model of asthma: effect of steroid treatment," *Am J Physiol Lung Cell Mol Physiol* Dec. 279 (6):L1120-1128.

Van Oosterhout, A.J., et al. (1993) "Effect of anti-IL-5 and IL-5 on airway hyperreactivity and eosinophils in guinea pigs," *Am Rev Respir Dis* Mar., 147(3):548-552.

Wilson (1993) "Vehicles for Gene Therapy," *Nature*, 365: 691-692.

Wood, K.V., et al. (1989) "Complementary DNA coding click beetle luciferases can elicit bioluminescence of different colors," *Science* 244:700-702.

Zhang, G., et al. (1999) "High levels of foreign gene expression in hepatocytes after tail vein injections of naked plasmid DNA," *Human Gene Therapy* 10:1735-1737.

Zhang W, et al. (2001) "Rapid in vivo functional analysis of transgenes in mice using whole body imaging of luciferase expression," *Transgenic Res.* Oct.:10(5):423-434.

GENBANK Accession No. AY015988.
protein Accession AAG54094.
mRNA sequence, GENBANK Accession No. AF272711.
protein sequence, GENBANK Accession No. AAG16224.
GENBANK Accession No. AY015995.
GENBANK Accession No. AF322221.
GENBANK Accession No. AF080431.
GENBANK Accession No. AF292560.
GENBANK Accession No. AF292559.
GENBANK Accession No. AF292558.
GENBANK Accession No. AF292557.
GENBANK Accession No. AF139645.
GENBANK Accession No. U47298.
GENBANK Accession No. U47297.
GENBANK Accession No. AY015994.
GENBANK Accession No. AF292556.
GENBANK Accession No. AJ011299.
GENBANK Accession No. U34588.
GENBANK Accession No. X06271.

FIGURE 1A (page 1 of 10)

```
ttctcagatg gtatgatttg acacagagct gggattatct ctgaaaggtt gtggggtgac    60
tttatgtatt aggctaaaca ccactccatg actctcagca gatgccaaat acctttaaat   120
tttgattttg tcactcagtg tggtggtcag atatgtttga aggcttcgtg gaaattagca   180
aaggttccgc ctctatggga ctgatgtaac tcagagaaac cagagaatac cacccggaga   240
gcaaaatgca ggctggcttg caatccccac atcctctcct gattaaactg ttaactttac   300
actctgactc tgacattcat gattttatgt gttttgagtt gctaacatgc aaaaatgcac   360
aactgtgggc cttttcttc ttttctattt tattttatta tttttattat ttaattaatt   420
ttttacactc catattttat tcccccatc caccctccaa ctgttccaca tcccatacct    480
cctccccacc ccctgtctc catgtggatg tccccacccc cgtcccacct gacctctaaa    540
ctccctgggg cctccagtct cttaagggtt aggtgcatca tctctgaatg aacacagacc   600
tgaaagtcct ctactgtatg tgtgttgggg gcctcatatc agctagtgta ccctgcctgt   660
ttgatggtct aatgtttgcg agatctcggg gtccagatta attgagactg ctggtgctcc   720
tataggatca cccttctcct cagcttcttt cagccttccc taattcaacc acagggtca   780 gctgcttctg tccactggtt gggtgcaaat atctgcatct gattctttca gctgcttgtt   840
gggtcttcca gagtgtggtc atgacaggtc ccttttttgta agctctccat agcctcagtg   900
atagagtcag gccttggaac cttcccttga gctggatctc actttgggcc tgtcgctgga   960
ccttcttttc ctcaatatcc tctccatttc catccctgta attctttcag acaggaacaa  1020
ttatgggtca gagatgtgac tgtgggatgg caacccatc cctcacttga tatcctgtct   1080
```

FIGURE 1A (page 2 of 10)

```
tcctgctgga ggtgggctct gtaatttccc tcttctactg tcctgcagtt catctaaggt 1140
cccttccttt gagtcccgag agtctctcac ctcccaggtt tctggtgctt tatggagggt 1200 cccccaacc ttctatctcc tgaggttgcc tgtttccatt ctttctgctg cccttaggg 1260 cttcagtcct tttccctcac ccaataccag atcaggttcc ccttcttccc cctccccc 1320 ccccggggg ggggcttttc ttatagagga actgtgttgg ttgtatgtgt gcactggaat 1380
gtatgagtat gcatgtgtgt gtgtgtgtgt gtgcatatgt atggaggcca gatgtcaacc 1440
ctggacattt ttttcttaga catggtcaat cttgctttaa atctttttt tttttaatta 1500 tttttaaatt gcgaatctat ttgtgcatgt gtgtgcagta cctattaagg ccagtagagg 1560
gctcaagagc tcccggagtt ggagttacag gcggttgtga attgccttag gagcttagga 1620
tgcttagaag ctctctctct ttgtttttga gacaagacaa gcgctttcat taggacttgg 1680
gacttgttga ttaggttcag tggccattgt acctcagggg tactccagcc tctccctccc 1740
caacacaggg gtgctgcctc gcctggctta aaaaaaaaat taaaattaaa aaaaaaatgt 1800
gggccgggca atagtggcac acacttttaa tctcagcact gggagacag aggcaggcag 1860 atctccaagt tccaggacag ccagagcagc taggcatggt gggacacatt ttcaatccca 1920
ccactgatga agcagaggta gatttctgta agttctatgt ggtaagttct gggacagcca 1980
gggatttttt tttttttttt agtgagtgcc tgcacacatg catgtgcatc gtgtgtgtct 2040
ggtacccaca gagggcatca gattgcctgg agttagcatt acaggtgttt ctgtgcttcc 2100
taactctgac tttggctttg tgtgtgagca gcaagtgctc ttagcttagg agccctctat 2160
```

FIGURE 1A (page 3 of 10)

```
ccagacctcc atgtctggtt tctcaggtgg tttccaggga tagaacttgg gtcctcctgt 2220
tcaagcagca agctctccct caccctatgc tggtccttta ttgaatacaa gtgagcccag 2280
gggacctgag gaggacgcag gcttccctgt cagattccca tcaacccta ctctggggc 2340 cttctttctc cacaagctca acagtcagcc tagcaatcct catccaggag gctgtatagg 2400
gaattcgtct ctccagacca gctgcagagt taggactgac ccttcctgcc ttttgctgac 2460
ttgattagca gttcagagag atcaagttct tgctcaaagc cacacaggtg ggtcaagcca 2520
tgacagaagt gggagtagtg ctggacttcc agccagctct ccagagcccc aagctgcact 2580
gtcagacttg gtgagtaaag gcaaggaact cagagctgtc ttttcagaac aacacacaca 2640
cacacacaca cacacacaca cacacacaca cacacacaca gagagagaga gagagagaga 2700
gagagagaga tgcagacaga tacacatata cagacacaca gacacataca tagacacata 2760
cacagttgca gacagacaca caaacagaca tatacagaca cacatataca gacacataca 2820
tagtcaaaca cacacccaga tgcagacaca cagacacata caaacacaca cacacacaga 2880
cacagaaact cagagacaca tacaaacaca cacacagata cacacagaaa cacagtcaca 2940
gacatacagg cacacagaga gacacacaca gaaacacaca gtgacacact cacacacaga 3000
cacaccatca tacacacaca gtggtgcaca cagacacatg cacacacagt gacacacaca 3060
gagagacaca cacacatcag cctctggcac agtgtgctgc cactaaggtt taggcaagct 3120 cccttttccat gcacatctca gtgttctcaa agttacacca ggacaaatga ccccctttcc 3180
aaagaaaccc tgggagcaag ggtgggtctg ccaagcctga gccttgctgt gtccctgtc 3240
```

FIGURE 1A (page 4 of 10)

```
ttaatggggc agttggagca gagcagataa agagatccga tcaggcctgt ggccagcagt 3300
tccaccatgg cgggtagaca gttcttgtga aagtgattgc agaaggatga ggtttcagac 3360
tgcccaggga ggaggggagg ggaggtcctc cagtgctgcc gattaagagt cctgagaaag 3420
aagctgtcct catggtccat ggcctggtct gccacagcat ccagtgaccc acagcaaggc 3480
tggtccaggg atggccctta ccataggtac tgggtcctga catgcacggg cacaaatcca 3540
tctcctgacc caacagcaat ggcaggcaag gtcacagcaa acacatctgc tccacaaatc 3600
ctaccaggcc tgccaggcac acctaggtag gaggctactg tgggcaaacg ccttttctgt 3660
gcggaacttg aggagcgtat tggattcata agcacatgat gaatttttgga aagaaactgt 3720 gagactaaga accagagggc ctaagcctgc cgagtcttgg aaggattccc tgtggatgag 3780
tgagacctag gaactcagtg ggagtcagcc aggcggagac aaagagcctt cagggcttgc 3840
gacttgtgtc tgtctgaaag atggtagact ttgctatgaa gctgaaagcc agtgtgctta 3900
ggaagcagag gaataggttt accctgcagg tgaggcagga gccagggttc tgagatggag 3960
ggagggaagc aggcagccca agcaagcaac tgaggagctg aatggtcagg gctccacatc 4020
ccaagcactc ctagaagcct tgtcacccca aaataataat ctcttcctca ccccttcct 4080 cctctttctc ctcagtgctg ggcatggaac gcagccttga gaatcgtccc agccctaagt 4140
acggtccccc tcacaggtcc tgagtggccc tgcctcattg tttttatttt ggccatttcc 4200
ctataggagg aagggcttgc ctgtgagatc cccaagccta tggccttgtc attgctggaa 4260
ggaaatgtat ctaccccaga agcaggttct gggttccact tgctgaggga agagctctca 4320
```

FIGURE 1A (page 5 of 10)

```
tatcagcctc atagacaggc agcttcccta acacccaacc aggaggatat acccctggct 4380
cctacttagt ggtctgcgca ccctctcttt tctctgctgg ttcaggctct gccctccacc 4440
ctggatctgt agcctaactg gcccctggag aaggaagaga actggagaaa tcccaactag 4500
gtcagggagg ggatttgttt tttcttgcta gggtggactt agtgggttaa gcaagaaagc 4560
tactcgctct cttctgagac ctggcccag gcctctgctg agtgttgact acacaccata 4620
gagatcaagt acggagcctc ttctcccacg cattcagaag accaatggac gtggtgacgt 4680
cattccttcg ttaaagttca atatgtgctg agaaacatca gtgctgagaa acatcactgt 4740
ggggtgcccc atagatcaaa gagggacatc agagatgtct ttggaggcga gcagaaagtg 4800
gccaacggaa ggccttctgg ctgaggttag ggtaaaatga gtggagttat tctggcaaca 4860
aggactgcgg atggatctag aagtggggga agggcacatc cattaaggct ggggtgtggt 4920
ggatggtggg gaggaacgat agtggaggct agggagaagc tgtgagcctg aggggtgtg 4980 gaagcattgg ggctcctgct gctcaataga ccaggtcact gtgcacccag cccttcccct 5040
ccctgggtgc tcagaaccca gtgattccct cctcactcaa aatacatgga ccggtgggtt 5100
gtggagggag tagaaagcct cctgttttgt cgctaatgaa ggagcaaagc gagctgttca 5160
cccttgcaca aaagctaagg ggttccgtga accccttgga gtcattaccc cagggaatca 5220
ttaaacaagg tcaggtggct cttgaggtcc actctgccgt tgttactcta aacaatcgca 5280
gcaataaaat tctcctcccc aagtacagtt tgtgccgctc tatatgctaa gtgattgctg 5340
ccaatactgt ttaactttaa taaccccgt gagttcaagt cagtgggttt ttttttttta 5400
```

FIGURE 1A (page 6 of 10)

```
ttgcgcataa gaaccgtggt taatttagga agttcccagt tatacaatgg ctgcctctgc 5460
tgtgtgcgtt tacttcaaga gtaaggacaa agctgtgcac gattgtattt acacatttca 5520
cttgcctggg gatgtatctc tgctgaaaga gtgcttcctt agcatacaca aggtcctggc 5580
aatccctggc accacatgaa ctgggggtgt gggtggggtg gaatatgcct gtaacccag 5640 cactgggtag gagtgattag gagaagccaa agttcaaggt catctttggc tacatagcaa 5700
gtttgaagct agcctagact acgtgaaacc ctgtctcaaa caaaacaaaa aatagttgat 5760
ataaatgata gcacagtact tataaagttg aaagaaatag aatctgattt ccttttaatt 5820
ctgttgttct acgtgaaggc tggcatttta attaatataa gattcaagtt taaaacagtg 5880
tgtgaaaact gtatctttta aaagatata ttttattaa gttttaactt cttgtagata 5940
tacacatatc tgtgtgtagg tgtgtgcata caggcgccct gggaatccag agaagggcat 6000
tggatcccct ggagctggag ttacaggcct ggaagctgtt gaatgtaggt gctgggaaca 6060
gaacccgggt cctctggaag tgctctaagc cactgagcca tctccccagc cctggaaaca 6120
gtatcttcct gtacaactga cttcacatgt gaaatggttt tacgggtttt ttatgccttc 6180
aagattgagc tgtttcttct ctttaaacgc ccgtttgtct gttttggga tgccctgct 6240 gcgtagctca gggcgatctc taactgcatc agtctcccac gtgttgggat ggcagcggtg 6300
tgccgccgca cctggtggaa ctgctgactc taaaactaaa gaagaaattt agtacttaac 6360
tatattttga atactaaagc tgctaatata agccaggtgt gtgtgttatc acacatctgt 6420
aattttggcc cttgggaggg ggaaggagga ggaagagttt caagccagcc aggacttcat 6480
```

FIGURE 1A (page 7 of 10)

```
gaggttctgt tccaaacacc taaaccaacc aaccaccacc accaccacca acaaaaatct 6540
aacaatatgt ggatatttcc ccttaagtta aaaacattaa gccattacat ttttcctttt 6600
atatagttag tatgtttgca tgcatgcatg tatttgttta tttccagagt ctcatgcatt 6660
ttagactgat ctctaacttc ctgtgtagct gtggcagacc ttgaacttca atctttcagc 6720
taatatatat tatgtattat atatatatgt atgtatgtat atatatatat ataatacata 6780
atatacacac atacatacat acacaatata tatatacaca cacatttata tatacacaca 6840
tacatacaca atatatatac atatacatat atatatacac atacacacat atacatatat 6900
attttactga cacaattata tacattaaga tcaataaaag aaaacctcct cacatttctg 6960
gccattacta tttgtttcat ttaatgagta tctttcaaaa ttatttttaat gggtagagga 7020 ggatactgaa ggaggcccta gtgtctgaca cacttcgttg ctactggaca aaacttagct 7080
acaaggaaaa tctctcctat gagttgctga gagaaaagac tcatgggaaa gcctgagaac 7140
ccatagtctt tgcccacact cctcccctgg tccctctgat cacgacaact aagaagaaag 7200
tcaatgtcag agctgactac catgagcatg tgcggaccct gcctgtctgt cagacctgtc 7260
acagtgaagg ccacagtggg tgcctaggct ggagggcacc tcaccttgtc cagggctcca 7320
tcttcatcag gtccctgtgg cctcagcccc agaactaggt gccaatgcct tcattttaga 7380
ggcctccctt ttagaaatct agccctgaag gatccaaaga cgcttttgca ttcttcgctc 7440
ctgcctccca gctgaagcca atggctgcct gaggggacag ccccgtgtaa aggtaacaaa 7500
gaagcaacaa taagatagaa caatgaggct tcttcagtgc cctgcttgcc aggcactgtg 7560
```

FIGURE 1A (page 8 of 10)

```
gtggtgtgtc acatgttcta ccaggagcta gggaaacctc cactgtgcag gagaaggcct 7620
ttaggcccag cacttgcctc acaggatgat gggattgtat caggagctct tgaggacttc 7680
tttgagctgc tctcagggg ctccttggtg ctgagtacag gatttaggtc ccagcttgat 7740
ttgagagggg gtcagacgtg gcatcctaga gggagctagg caaagggat ggcattcatc 7800 aaagggagag gatcataaac agaagattag catggttggt gctctggaca gggtcccgta 7860
ggagagcagc tgagtgtaag gtgaagggag cacgtggccc caggggttag aagagccatg 7920
tgacaagcca tacttcttca gtctcctgaa tgagctttac ccactagtcc agacccaaga 7980
ggcagcttaa gcaacatccc cagaacttgc cttccacagt cagggtctgt agggtccctc 8040
aggctctcag tcaaatcttt aagcctaact tgttaagata cccaaatata acaaatgtag 8100
caggtaggga tggatctaga gcccagtgct ctgcccctgg ttcatccccc aaactcactg 8160
cattccatcg ctaggaccac tctcaactaa ctggctgctg ttaaagaact aatgacccct 8220
ttaggggaga gcagagttct gtgggggtat ggcgtccctg gaaggagggc atcctagctc 8280
tagcctgggg catctggagg ggagggaaag ctcagctgtg catggtaccg tttaaaatct 8340
cttgggatca ccattctggc tcttaagctt ggaaacggag gtctagcagg gtatgtcggg 8400
agatctagtc gaccttcatc cttccttgta attttgtatc ccttggcaaa caggttcggc 8460
ctctgctgaa gatggagat aagatagggg aagccttgcc aacaggagct tgtgaaagga 8520
gttgctaaag caaaatggct gtttcaggag caactgttga ggccggtggc agaggaggga 8580
gcactgatga gggaggagga agcactgatg cgggaggagg ggcaggggaa ggcgttgtgc 8640
```

FIGURE 1A (page 9 of 10)

```
aggttgaggt gggacagggg ttgaagagcc cggggaagag tctcctgagg tctaggaagg 8700
aatggacatg ctcacctgaa gggaccagga taggttggtt accagcacag tggcagtggc 8760
tttggagcca gagaccaaca ctagccatca aggcaggcaa ggatcaacag gctcctccag 8820
agaagggcct gtcagaagga aaggcttgaa agtgtgaagg aaggagctgc ggcccgactg 8880
agttgagttc tgcccaagat ctcactgcct gtgaaagagc cagatggaga ctcaggtcag 8940
tcaggcctag tgcagcaatc tctttcacgg gagcacacag taagcccacc actgctgtgc 9000
attgagagga gatcagggca cgctcagagc cacagtgagc ctttaggtct gggcaggaag 9060
cttccagcag ttcactcgct gtgagttcta cctgtgacac ctcaccatga ccccaggtgt 9120
cccctgaggt atttctctgg catcttggag ggagcagatc gccctaggga gataaggaga 9180
gaactggatt attgacgact cactcctcta caaacattta atgaacgcct actgaatgga 9240
gccttgtgct gagtattagg ggtatggtaa tatgtctgga ccccctttct gccctgatgg 9300
ggagagagga acctttccaa acatccacac aaaacctatt ttagggatgt gaaaatgagt 9360
gacaattagc gatggggcca agctctctct ttttgtcagt aacgaggtca ttcatcactc 9420
attgggtgac acctccatcc ccagcactgc ttcgggttgt gggggcaaa tgcatccatg 9480 aacccaagac tagaggtggg tgtggaacaa ggtaatggtg gctaggggag cccccattct 9540
ggtgagttgg taaagtatga tggggtgtt tcaatcccac agcggctccc cctgaaaatc 9600
agagcgaggt tccagagctc cgccttaggg gttgggcttc tggcagccaa gtaccgcccc 9660
ttctacccca agatgggata taaagtctct tagctccttc cagagaagag taagaagaaa 9720
```

FIGURE 1A (page 10 of 10)

```
gaaaccatca caggacctct aaggaagaga ggaattgtac actcacctcc gtggcatctg    9780
tgggcattgc ttgcctgctt agctgtagcg gggggttcag cttgcatg                 9828
```

FIGURE 1B (page 1 of 9)

```
ttctcagatg gtatgatttg acacagagct gggattatct ctgaaaggtt gtggggtgac    60
tttatgtatt aggctaaaca ccactccatg actctcagca gatgccaaat acctttaaat   120
tttgattttg tcactcagtg tggtggtcag atatgtttga aggcttcgtg gaaattagca   180
aaggttccgc ctctatggga ctgatgtaac tcagagaaac cagagaatac cacccggaga   240
gcaaaatgca ggctggcttg caatccccac atcctctcct gattaaactg ttaactttac   300
actctgactc tgacattcat gattttatgt gttttgagtt gctaacatgc aaaaatgcac   360
aactgtgggc cttttcttc ttttctattt tattttatta tttttattat ttaattaatt   420
ttttacactc catattttat tccccccatc caccctccaa ctgttccaca tcccatacct   480
cctccccacc ccctgtctc catgtggatg tccccacccc cgtcccacct gacctctaaa   540
ctccctgggg cctccagtct cttaagggtt aggtgcatca tctctgaatg aacacagacc   600
tgaaagtcct ctactgtatg tgtgttgggg gcctcatatc agctagtgta ccctgcctgt   660
ttgatggtct aatgtttgcg agatctcggg gtccagatta attgagactg ctggtgctcc   720
tataggatca cccttctcct cagcttcttt cagccttccc taattcaacc acagggtca   780 gctgcttctg tccactggtt gggtgcaaat atctgcatct gattctttca gctgcttgtt   840
gggtcttcca gagtgtggtc atgacaggtc ccttttgta agctctccat agcctcagtg   900
atagagtcag gccttggaac cttcccttga gctggatctc actttgggcc tgtcgctgga   960 ccttctttc ctcaatatcc tctccatttc catccctgta attctttcag acaggaacaa  1020
ttatgggtca gagatgtgac tgtgggatgg caaccccatc cctcacttga tatcctgtct  1080
```

FIGURE 1B (page 2 of 9)

```
tcctgctgga ggtgggctct gtaatttccc tcttctactg tcctgcagtt catctaaggt 1140
cccttccttt gagtcccgag agtctctcac ctcccaggtt tctggtgctt tatggagggt 1200 cccccaacc ttctatctcc tgaggttgcc tgtttccatt ctttctgctg cccttaggg 1260 cttcagtcct tttccctcac ccaataccag atcaggttcc ccttcttccc cctccccc 1320 ccccggggg ggggcttttc ttatagagga actgtgttgg ttgtatgtgt gcactggaat 1380
gtatgagtat gcatgtgtgt gtgtgtgtgt gtgcatatgt atggaggcca gatgtcaacc 1440
ctggacattt ttttcttaga catggtcaat cttgctttaa atctttttt tttttaatta 1500 tttttaaatt gcgaatctat ttgtgcatgt gtgtgcagta cctattaagg ccagtagagg 1560
gctcaagagc tcccggagtt ggagttacag gcggttgtga attgccttag gagcttagga 1620
tgcttagaag ctctctctct ttgttttga gacaagacaa gcgctttcat taggacttgg 1680
gacttgttga ttaggttcag tggccattgt acctcagggg tactccagcc tctccctccc 1740
caacacaggg gtgctgcctc gcctggctta aaaaaaaat taaaattaaa aaaaaaatgt 1800
gggccgggca atagtggcac acacttttaa tctcagcact tgggagacag aggcaggcag 1860
atctccaagt tccaggacag ccagagcagc taggcatggt gggacacatt ttcaatccca 1920
ccactgatga agcagaggta gatttctgta agttctatgt ggtaagttct gggacagcca 1980 gggattttt tttttttttt agtgagtgcc tgcacacatg catgtgcatc gtgtgtgtct 2040
ggtacccaca gagggcatca gattgcctgg agttagcatt acaggtgttt ctgtgcttcc 2100
taactctgac tttggctttg tgtgtgagca gcaagtgctc ttagcttagg agccctctat 2160
```

FIGURE 1B (page 3 of 9)

```
ccagacctcc atgtctggtt tctcaggtgg tttccaggga tagaacttgg gtcctcctgt 2220
tcaagcagca agctctccct caccctatgc tggtccttta ttgaatacaa gtgagcccag 2280
gggacctgag gaggacgcag gcttccctgt cagattccca tcaacccta ctctgggggc 2340 cttctttctc cacaagctca acagtcagcc tagcaatcct catccaggag gctgtatagg 2400
gaattcgtct ctccagacca gctgcagagt taggactgac ccttcctgcc ttttgctgac 2460
ttgattagca gttcagagag atcaagttct tgctcaaagc cacacaggtg ggtcaagcca 2520
tgacagaagt gggagtagtg ctggacttcc agccagctct ccagagcccc aagctgcact 2580
gtcagacttg gtgagtaaag gcaaggaact cagagctgtc ttttcagaac aacacacaca 2640
cacacacaca cacacacaca cacacacaca cacacacaca gagagagaga gagagagaga 2700
gagagagaga tgcagacaga tacacatata cagacacaca gacacataca tagacacata 2760
cacagttgca gacagacaca caaacagaca tatacagaca cacatataca gacacataca 2820
tagtcaaaca cacacccaga tgcagacaca cagacacata caaacacaca cacacacaga 2880
cacagaaact cagagacaca tacaaacaca cacacagata cacacagaaa cacagtcaca 2940
gacatacagg cacacagaga gacacacaca gaaacacaca gtgacacact cacacacaga 3000
cacaccatca tacacacaca gtggtgcaca cagacacatg cacacacagt gacacacaca 3060
gagagacaca cacacatcag cctctggcac agtgtgctgc cactaaggtt taggcaagct 3120
ccctttccat gcacatctca gtgttctcaa agttacacca ggacaaatga cccccttccc 3180
aaagaaaccc tgggagcaag ggtgggtctg ccaagcctga gccttgctgt gtccctgtc 3240
```

FIGURE 1B (page 4 of 9)

```
ttaatggggc agttggagca gagcagataa agagatccga tcaggcctgt ggccagcagt 3300
tccaccatgg cgggtagaca gttcttgtga aagtgattgc agaaggatga ggtttcagac 3360
tgcccaggga ggaggggagg ggaggtcctc cagtgctgcc gattaagagt cctgagaaag 3420
aagctgtcct catggtccat ggcctggtct gccacagcat ccagtgaccc acagcaaggc 3480
tggtccaggg atggcccta ccataggtac tgggtcctga catgcacggg cacaaatcca 3540
tctcctgacc caacagcaat ggcaggcaag gtcacagcaa acacatctgc tccacaaatc 3600
ctaccaggcc tgccaggcac acctaggtag gaggctactg tgggcaaacg cctttttctgt 3660 gcggaacttg aggagcgtat tggattcata agcacatgat gaatttttgga aagaaactgt 3720 gagactaaga accagagggc ctaagcctgc cgagtcttgg aaggattccc tgtggatgag 3780
tgagacctag gaactcagtg ggagtcagcc aggcggagac aaagagcctt cagggcttgc 3840
gacttgtgtc tgtctgaaag atggtagact ttgctatgaa gctgaaagcc agtgtgctta 3900
ggaagcagag gaataggttt accctgcagg tgaggcagga gccagggttc tgagatggag 3960
ggagggaagc aggcagccca agcaagcaac tgaggagctg aatggtcagg gctccacatc 4020
ccaagcactc ctagaagcct tgtcacccca aaataataat ctcttcctca ccccttcct 4080 cctctttctc ctcagtgctg ggcatggaac gcagccttga gaatcgtccc agccctaagt 4140
acggtccccc tcacaggtcc tgagtggccc tgcctcattg tttttatttt ggccatttcc 4200
ctataggagg aagggcttgc ctgtgagatc cccaagccta tggccttgtc attgctggaa 4260
ggaaatgtat ctaccccaga agcaggttct gggttccact tgctgaggga agagctctca 4320
```

FIGURE 1B (page 5 of 9)

```
tatcagcctc atagacaggc agcttccta acacccaacc aggaggatat accccctggct 4380 cctacttagt ggtctgcgca ccctctcttt tctctgctgg ttcaggctct gccctccacc 4440
ctggatctgt agcctaactg gcccctggag aaggaagaga actggagaaa tcccaactag 4500
gtcagggagg ggatttgttt tttcttgcta gggtggactt agtgggttaa gcaagaaagc 4560
tactcgctct cttctgagac ctggccccag gcctctgctg agtgttgact acacaccata 4620
gagatcaagt acggagcctc ttctcccacg cattcagaag accaatggac gtggtgacgt 4680
cattccttcg ttaaagttca atatgtgctg agaaacatca gtgctgagaa acatcactgt 4740
ggggtgcccc atagatcaaa gagggacatc agagatgtct ttggaggcga gcagaaagtg 4800
gccaacggaa ggccttctgg ctgaggttag ggtaaaatga gtggagttat tctggcaaca 4860
aggactgcgg atggatctag aagtggggga agggcacatc cattaaggct ggggtgtggt 4920
ggatggtggg gaggaacgat agtggaggct agggagaagc tgtgagcctg aggggtgtg 4980 gaagcattgg ggctcctgct gctcaataga ccaggtcact gtgcacccag cccttcccct 5040
ccctgggtgc tcagaaccca gtgattccct cctcactcaa aatacatgga ccggtgggtt 5100
gtggagggag tagaaagcct cctgttttgt cgctaatgaa ggagcaaagc gagctgttca 5160
cccttgcaca aaagctaagg ggttccgtga accccttgga gtcattaccc cagggaatca 5220
ttaaacaagg tcaggtggct cttgaggtcc actctgccgt tgttactcta aacaatcgca 5280
gcaataaaat tctcctcccc aagtacagtt tgtgccgctc tatatgctaa gtgattgctg 5340
ccaatactgt ttaactttaa taaccccgt gagttcaagt cagtgggttt ttttttttta 5400
```

FIGURE 1B (page 6 of 9)

```
ttgcgcataa gaaccgtggt taatttagga agttcccagt tatacaatgg ctgcctctgc 5460
tgtgtgcgtt tacttcaaga gtaaggacaa agctgtgcac gattgtattt acacatttca 5520
cttgcctggg gatgtatctc tgctgaaaga gtgcttcctt agcatacaca aggtcctggc 5580
aatccctggc accacatgaa ctgggggtgt gggtggggtg gaatatgcct gtaacccag 5640 cactgggtag gagtgattag gagaagccaa agttcaaggt catctttggc tacatagcaa 5700
gtttgaagct agcctagact acgtgaaacc ctgtctcaaa caaaacaaaa aatagttgat 5760
ataaatgata gcacagtact tataaagttg aaagaaatag aatctgattt ccttttaatt 5820
ctgttgttct acgtgaaggc tggcatttta attaatataa gattcaagtt taaaacagtg 5880
tgtgaaaact gtatctttta aaagatata ttttattaa gttttaactt cttgtagata 5940
tacacatatc tgtgtgtagg tgtgtgcata caggcgccct gggaatccag agaagggcat 6000
tggatcccct ggagctggag ttacaggcct ggaagctgtt gaatgtaggt gctgggaaca 6060
gaacccgggt cctctggaag tgctctaagc cactgagcca tctccccagc cctggaaaca 6120
gtatcttcct gtacaactga cttcacatgt gaaatggttt tacgggtttt ttatgccttc 6180
aagattgagc tgtttcttct ctttaaacgc ccgtttgtct gttttggga tgcccctgct 6240 gcgtagctca gggcgatctc taactgcatc agtctcccac gtgttgggat ggcagcggtg 6300
tgccgccgca cctggtggaa ctgctgactc taaaactaaa gaagaaattt agtacttaac 6360
tatattttga atactaaagc tgctaatata agccaggtgt gtgtgttatc acacatctgt 6420 aatttggcc cttgggaggg ggaaggagga ggaagagttt caagccagcc aggacttcat 6480
```

FIGURE 1B (page 7 of 9)

```
gaggttctgt tccaaacacc taaaccaacc aaccaccacc accaccacca acaaaaatct 6540
aacaatatgt ggatatttcc ccttaagtta aaaacattaa gccattacat ttttcctttt 6600
atatagttag tatgtttgca tgcatgcatg tatttgttta tttccagagt ctcatgcatt 6660
ttagactgat ctctaacttc ctgtgtagct gtggcagacc ttgaacttca atctttcagc 6720
taatatatat tatgtattat atatatatgt atgtatgtat atatatatat ataatacata 6780
atatacacac atacatacat acacaatata tatatacaca cacatttata tatacacaca 6840
tacatacaca atatatatac atatacatat atatatacac atacacacat atacatatat 6900
attttactga cacaattata tacattaaga tcaataaaag aaaacctcct cacatttctg 6960
gccattacta tttgtttcat ttaatgagta tctttcaaaa ttatttaat gggtagagga 7020 ggatactgaa ggaggcccta gtgtctgaca cacttcgttg ctactggaca aaacttagct 7080
acaaggaaaa tctctcctat gagttgctga gagaaaagac tcatgggaaa gcctgagaac 7140
ccatagtctt tgcccacact cctcccctgg tccctctgat cacgacaact aagaagaaag 7200
tcaatgtcag agctgactac catgagcatg tgcggaccct gcctgtctgt cagacctgtc 7260
acagtgaagg ccacagtggg tgcctaggct ggagggcacc tcaccttgtc cagggctcca 7320
tcttcatcag gtccctgtgg cctcagcccc agaactaggt gccaatgcct tcatttaga 7380 ggcctccctt ttagaaatct agccctgaag gatccaaaga cgcttttgca ttcttcgctc 7440
ctgcctccca gctgaagcca atggctgcct gagggacag ccccgtgtaa aggtaacaaa 7500
gaagcaacaa taagatagaa caatgaggct tcttcagtgc cctgcttgcc aggcactgtg 7560
```

FIGURE 1B (page 8 of 9)

```
gtggtgtgtc acatgttcta ccaggagcta gggaaacctc cactgtgcag gagaaggcct 7620
ttaggcccag cacttgcctc acaggatgat gggattgtat caggagctct tgaggacttc 7680
tttgagctgc tctcagggggg ctccttggtg ctgagtacag gatttaggtc ccagcttgat 7740
ttgagagggg gtcagacgtg gcatcctaga gggagctagg caaaggggat ggcattcatc 7800
aaagggagag gatcataaac agaagattag catggttggt gctctggaca gggtcccgta 7860
ggagagcagc tgagtgtaag gtgaagggag cacgtggccc caggggttag aagagccatg 7920
tgacaagcca tacttcttca gtctcctgaa tgagctttac ccactagtcc agacccaaga 7980
ggcagcttaa gcaacatccc cagaacttgc cttccacagt cagggtctgt agggtccctc 8040
aggctctcag tcaaatcttt aagcctaact tgttaagata cccaaatata acaaatgtag 8100
caggtaggga tggatctaga gcccagtgct ctgcccctgg ttcatccccc aaactcactg 8160
cattccatcg ctaggaccac tctcaactaa ctggctgctg ttaaagaact aatgacccct 8220
ttagggagga gcagagttct gtggggtat ggcgtccctg gaaggagggc atcctagctc 8280
tagcctgggg catctggagg ggagggaaag ctcagctgtg catggtaccg tttaaaatct 8340
cttgggatca ccattctggc tcttaagctt ggaaacggag gtctagcagg gtatgtcggg 8400
agatctagtc gaccttcatc cttccttgta attttgtatc ccttggcaaa caggttcggc 8460
ctctgctgaa gatgggagat aagatagggg aagccttgcc aacaggagct tgtgaaagga 8520
gttgctaaag caaaatggct gtttcaggag caactgttga ggccggtggc agaggaggga 8580
gcactgatga gggaggagga agcactgatg cgggaggagg ggcaggggaa ggcgttgtgc 8640
```

FIGURE 1B (page 9 of 9)

```
aggttgaggt gggacagggg ttgaagagcc cggggaagag tctcctgagg tctaggaagg 8700
aatggacatg ctcacctgaa gggaccagga taggttggtt accagcacag tggcagtggc 8760
tttggagcca gagaccaaca ctagccatca aggcaggcaa ggatcaacag gctcctccag 8820
agaagggcct gtcagaagga aaggcttgaa agtgtgaagg aaggagctgc ggcccgactg 8880
agttgagttc tgcccaagat ctcactgcct gtgaaagagc cagatggaga ctcaggtcag 8940
tcaggcctag tgcagcaatc tctttcacgg gagcacacag taagcccacc actgctgtgc 9000
attgagagga gatcagggca cgctcagagc cacagtgagc ctttaggtct gggcaggaag 9060
cttccagcag ttcactcgct gtgagttcta cctgtgacac ctcaccatga ccccaggtgt 9120
cccctgaggt atttctctgg catcttggag ggagcagatc gccctaggga gataaggaga 9180
gaactggatt attgacgact cactcctcta caaacattta atgaacgcct actgaatgga 9240
gccttgtgct gagtattagg ggtatggtaa tatgtctgga ccccctttct gccctgatgg 9300
ggagagagga acctttccaa acatccacac aaaacctatt ttagggatgt gaaaatgagt 9360
gacaattagc gatggggcca agctctctct ttttgtcagt aacgaggtca ttcatcactc 9420
attgggtgac acctccatcc ccagcactgc                                  9450
```

ISOLATION AND IDENTIFICATION OF TRANSCRIPTION CONTROL ELEMENTS ASSOCIATED WITH MOUSE EOSINOPHIL PEROXIDASE EXPRESSION

This application is a divisional of U.S. patent application Ser. No. 10/126,912, filed Apr. 19, 2002 and issued Feb. 22, 2005 as U.S. Pat. No. 6,858,773, which is related to U.S. Provisional Application Ser. No. 60/285,603, filed 20 Apr. 2001, and from which priority is claimed under 35 USC 119(e)(1), and which the specifications of the applications are hereby incorporated by reference in their entireties.

FIELD OF THE INVENTION

The present invention relates generally to the field of molecular biology and medicine. In particular, the invention relates to transcription control elements derived from the genomic locus of the murine eosinophil peroxidase (EPX) gene, and methods of use thereof. The invention further relates to isolated polynucleotides in regulatory regions of the murine EPX gene, to reporter constructs comprising those isolated polynucleotides, to cells transformed with those reporter constructs, and to transgenic animals comprising those reporter constructs. The invention further relates to in vivo assay methods that employ animals transfected with such reporter constructs, and/or transgenic animals comprising such constructs.

BACKGROUND OF THE INVENTION

Eosinophils play a protective role in host immunity to parasitic worm infections and, detrimentally, are involved in the pathophysiology of asthma and other allergic diseases. Eosinophils are prominent in airway inflammation. Eosinophils are involved in diseases like asthma, chronic eosinophilic pneumonia, Churg-Strauss Syndrome, Hypereosinophilic syndrome, allergic rhinitis, atopic dermatitis.

The present invention relates to constructs and methods to mark the eosinophils in vivo and also to methods for directly monitoring EPX gene regulation in real-time in live animals.

BRIEF DESCRIPTION OF THE DRAWINGS

FIG. 1A (SEQ ID NO:1) comprises the nucleotide sequence of a transcriptional control element from the mouse eosinophil peroxidase (EPX) gene locus. In the figure, the sequence represents 9,828 nucleotides in total, the translational start codon (ATG) is located at positions 9,826–9,828, a TATA box is located at positions 9,679–9,682, a major transcription start site begins with the A at position 9,709. A novel approximately 9.5 kb region of the EPX gene locus is from nucleotide position 1 to 9,450 of FIG. 1A and the approximately 9.5 kb sequence is presented alone in FIG. 1B (SEQ ID NO:2).

SUMMARY OF THE INVENTION

Figure 2:
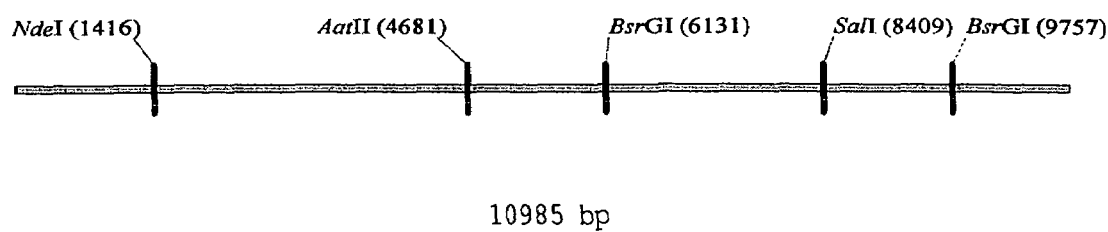
FIG. 2 presents a restriction map of an XbaI fragment (10,985 base pairs) derived from a BAC-mouse genomic clone that comprises the EPX transcriptional control elements described herein.

The present invention relates to novel transcription control elements derived from the genomic locus of the murine eosinophil peroxidase (EPX) gene. The present invention comprises isolated polynucleotides, expression cassettes, vectors, recombinant cells, and transgenic, non-human animals that comprise the transcription control elements described herein.

In one aspect, the present invention relates to a transgenic rodent comprising, an expression cassette wherein the expression cassette comprises a polynucleotide derived from the mouse eosinophil peroxidase gene, wherein the polynucleotide is operably linked to a coding sequence of interest. Typically the polynucleotide comprises at least one transcriptional control element. Further, eosinophils from the transgenic animal express the coding sequence of interest at a greater level than other, non-eosinophil blood cell-types. The polynucleotide has, for example, at least 95% or greater identity to nucleotides 1–9,825 of SEQ ID NO:1. Alternately, the polynucleotide has at least 95% or greater identity to SEQ ID NO:2, or at least 95% or greater identity to SEQ ID NO:7. In one embodiment, the polynucleotide consists of a polynucleotide having at least 95% or greater identity to nucleotides 1–9,825 of SEQ ID NO:1. In a further embodiment, the polynucleotide consists of a polynucleotide having at least 95% or greater identity to SEQ ID NO:2. In yet another embodiment, the polynucleotide consists of a polynucleotide having at least 95% or greater identity to SEQ ID NO:7.

In another aspect of the present invention, the transgenic rodent shows induction of the expression of the coding sequence of interest following ovalbumin challenge via intraperitoneal injection or via airway inhalation.

In another aspect of the present invention, administration of IL-5 to the transgenic rodent promotes greater trafficking of eosinophils to the esophagus of the transgenic rodent than to other regions of the body of the transgenic rodent, and the trafficking is monitored by tracking expression of the coding sequence of interest.

In a further aspect of the present invention, greater basal expression of the coding sequence of interest is seen in the lamina propria of the transgenic rodent relative to basal expression of the coding sequence of interest in other regions of the body of the transgenic rodent.

In yet a further aspect of the present invention, expression of the coding sequence of interest is induced in the transgenic rodent when IL-5 is over-expressed in the transgenic animal.

Further, in another aspect of the present invention, levels of expression of the coding sequence of interest after allergen-induction are higher before treatment with a glucocorticoid than after treatment with the glucocorticoid. One exemplary glucocorticoid is dexamethasone.

The coding sequence of interest in the transgenic rodent may, for example, be a reporter gene (or reporter sequence). One exemplary reporter sequence encodes a light-generating protein (e.g., a bioluminescent protein or a fluorescent protein). In one embodiment, the reporter sequence encodes the bioluminescent protein luciferase. In another embodiment, the reporter sequence encodes a fluorescent protein, including, but not limited to, blue fluorescent protein, cyan fluorescent protein, green fluorescent protein, yellow fluorescent protein, and/or red fluorescent protein.

The transgenic rodent of the present invention may, for example, be a mouse, rat, gerbil, hamster, or guinea pig.

The present invention also includes methods employing the transgenic animals of the present invention. One exemplary method is for identifying an analyte that modulates expression of a reporter sequence. Expression of the reporter sequence is mediated by transcription control elements derived from a mouse eosinophil peroxidase gene. The method is typically carried out in a transgenic, intact, living rodent. The analyte is administered to the transgenic, living rodent. Expression of the reporter sequence is monitored wherein an effect on the level of expression of the reporter sequence indicates that the analyte affects expression mediated by transcription control elements derived from the mouse eosinophil peroxidase gene.

Another method relates to monitoring eosinophil cell location in a living, transgenic rodent. In the method eosinophil production is induced in the living, transgenic rodent. Eosinophil cell location is monitored in the living, transgenic rodent by monitoring locations of expression of the reporter sequence in regions of the body of the living, transgenic rodent. The monitoring may be carried out over a series of time intervals. The monitoring may be begun before, during, or after inducing eosinophil production.

A further method relates to evaluating the effect of an analyte on eosinophil migration in a living, transgenic rodent. In the method, eosinophil migration is induced at a selected site in first and second living, transgenic rodents. An analyte is administered to the first living, transgenic rodent. Eosinophil migration to the selected site in the first and second living, transgenic rodents is monitored by monitoring expression of the reporter sequence in the living, transgenic rodents. Any effect of the analyte on eosinophil migration in a living, transgenic rodent is evaluated by comparing eosinophil migration in the first and second living, transgenic rodents.

Yet another method relates to inducing eosinophil, cell-type specific expression of a coding sequence of interest in a transgenic mouse. In this method eosinophil production is induced in a living, transgenic rodent, wherein the induction of eosinophil production results in eosinophil, cell-type specific expression of the coding sequence of interest in the transgenic rodent.

In yet a further aspect, the invention relates to transcription control elements derived from the genomic locus of the murine eosinophil peroxidase (EPX) gene, wherein the transcription control elements are associated with a reporter sequence. In particular, recombinant nucleic acid molecules comprising SEQ ID NO:1, SEQ ID NO:2, and SEQ ID NO:7, as well as fragments thereof, are described. The invention further relates to in vivo assay methods that employ animals transfected with such reporter constructs.

In one aspect, the present invention includes isolated polynucleotides and/or expression cassettes comprising a polynucleotide having at least about 95% identity to the sequence of SEQ ID NO:2, or fragments thereof, operably linked to a coding sequence of interest, wherein the polynucleotide or fragments thereof comprise at least one transcriptional control element.

In some embodiments the coding sequence of interest is a reporter sequence, for example, a light-generating protein. Such light-generating proteins comprise bioluminescent proteins (including but not limited to, procaryotic or eucaryotic luciferase) and fluorescent proteins (including but not limited to, blue fluorescent protein, cyan fluorescent protein, green fluorescent protein, yellow fluorescent protein, and red fluorescent protein, as well as, enhanced and/or destabilized variants thereof).

The present invention also includes vectors comprising the isolated polynucleotides and/or expression cassettes of the present invention. Such vectors typically include a vector backbone, and may be linear or circular, comprise one or more origins of replication (e.g., a shuttle vector), be site-specifically or randomly integrating, and comprise one or more selectable or screenable markers.

In one embodiment the present invention includes cells comprising the expression cassettes and/or vectors of the present invention, e.g., eosinophil cells and/or precursors thereof. In another embodiment, transgenic, non-human, animals (e.g., rodents, including, but not limited to, mice, rats, hamsters, gerbils, and guinea pigs) may comprise the expression cassettes and/or vectors or the present invention. In a further embodiment, the present invention includes non-human animals that comprise a subset of cells comprising the expression cassettes and/or vectors of the present invention, for example, non-human animals into which eosinophil cells, or precursors thereof, comprising an expression cassette of the present invention, have been introduced. Such non-human animals may be generated, for example, by administration of the eosinophils, comprising expression cassettes and/or vectors of the present invention, via intravenous injection.

In yet another aspect, the present invention includes methods of using the expression cassettes, vectors, cells, and non-human animals of the present invention. In one embodiment, the invention includes a method for identifying an analyte capable of modulating expression of a murine eosinophil peroxidase (EPX) gene in a transgenic, living, non-human animal. Such a method typically comprises administering to the animal an analyte. The animal comprises one or more of the expression cassettes or vectors of the present invention typically including a reporter sequence. Expression of the reporter sequence is monitored. An effect on the expression of the reporter sequence, which is mediated by the analyte, indicates that the analyte affects expression of the gene corresponding to the transcriptional control elements which comprise the expression cassettes and/or vectors employed in the method.

Another method comprises identifying an analyte capable of modulating expression of a murine eosinophil peroxidase (EPX) gene in a living, non-human animal. In this method, a mixture comprising eosinophil cells, or precursors thereof, comprising an expression cassette of the present invention typically including a reporter sequence, is administered to the animal concomitant with, before, or after administration of an analyte. Expression of the reporter sequence is monitored. An effect on the expression of the reporter sequence, which is mediated by the analyte, indicates that the analyte affects expression of gene corresponding to the transcriptional control elements which comprise the expression cassettes and/or vectors employed in the method. In one embodiment the mixture is administered by intravenous injection.

In a further embodiment of the present invention, the expression cassettes comprising the transcription control elements of the present invention and a reporter, are used to monitor the expression of the murine eosinophil peroxidase (EPX) gene in a cell. In this embodiment expression of a reporter sequence is monitored in the cell and expression of the reporter sequence corresponds to expression of gene corresponding to the transcriptional control elements which comprise the expression cassettes and/or vectors employed in the method.

In yet another aspect of the present invention, the location and/or migration of labeled eosinophil cells (e.g., carrying an expression cassette of the present invention comprising a reporter gene) are monitored in a living, non-human animal. The animal may be a transgenic animal or an animal into which label cells have been introduced. In one embodiment, the present invention describes a method for monitoring eosinophil cell location in a living, transgenic animal, e.g., a rodent, by inducing eosinophil production in a living, transgenic rodent comprising an expression cassette of the present invention. The location of eosinophil cells are monitored, e.g., temporally and spatially, in the living, transgenic rodent by monitoring locations of expression of the reporter sequence in the living, transgenic rodent. Monitoring of the animal may begin before, during, or concurrently with inducement of eosinophil production.

In a further embodiment, the present invention comprises a method for evaluating the effect of an analyte on eosinophil migration in a living, transgenic rodent. In this method eosinophil migration is induced at a selected site in first and second living, transgenic animals, each comprising an expression cassette, comprising a reporter sequence, of the present invention. The analyte is administered to the first living, transgenic animal. Eosinophil migration is monitored, as described herein, to the selected site in the first and second living, transgenic animals by monitoring expression of the reporter sequence in the living, transgenic animals. Any effect of the analyte on eosinophil migration is evaluated in the living, transgenic animals by comparing eosinophil migration in the first and second living, transgenic animals.

In a further embodiment of the present invention, a method for inducing eosinophil, cell-type specific expression of a coding sequence of interest in a transgenic, non-human animal is described. In this method eosinophil production is induced in a living, transgenic, non-human animal, comprising an expression cassette of the present invention, wherein the coding sequence of interest is operably linked to a polynucleotide of the present invention, or fragments thereof, that comprise at least one eosinophil, cell-type specific transcriptional control element. The induction of eosinophil production results in eosinophil, cell-type specific expression of the coding sequence of interest in the transgenic animal.

These and other embodiments of the present invention will readily occur to those of ordinary skill in the art in view of the disclosure herein.

DETAILED DESCRIPTION OF THE INVENTION

The practice of the present invention will employ, unless otherwise indicated, conventional techniques of molecular biology, microbiology, cell biology and recombinant DNA, which are within the skill of the art. See, e.g., Sambrook, Fritsch, and Maniatis, MOLECULAR CLONING: A LABORATORY MANUAL, 2nd edition (1989); CURRENT PROTOCOLS IN MOLECULAR BIOLOGY, (F. M. Ausubel et al. eds., 1987); the series METHODS IN ENZYMOLOGY (Academic Press, Inc.); PCR 2: A PRACTICAL APPROACH (M. J. McPherson, B. D. Hames and G. R. Taylor eds., 1995); ANIMAL CELL CULTURE (R. I. Freshney. Ed., 1987); "Transgenic Animal Technology: A Laboratory Handbook," by Carl A. Pinkert, (Editor) First Edition, Academic Press; ISBN: 0125571658; and "Manipulating the Mouse Embryo: A Laboratory Manual," Brigid Hogan, et al., ISBN: 0879693843, Publisher: Cold Spring Harbor Laboratory Press, Pub. Date: September 1999, Second Edition.

All publications, patents and patent applications cited herein, whether supra or infra, are hereby incorporated by reference in their entirety.

1. Definitions

In describing the present invention, the following terms will be employed, and are intended to be defined as indicated below. Unless otherwise indicated, all terms used herein have the same meaning as they would to one skilled in the art of the present invention.

The terms "nucleic acid molecule" and "polynucleotide" are used interchangeably to and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term polynucleotide sequence is the alphabetical representation of a polynucleotide molecule. This alphabetical representation can be input into databases in a computer having a central processing unit and used for bioinformatics applications such as functional genomics and homology searching.

A "coding sequence" or a sequence which "encodes" a selected polypeptide, is a nucleic acid molecule which is transcribed (in the case of DNA) and translated (in the case of mRNA) into a polypeptide, for example, in vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence. "Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences, which are immunologically identifiable with a polypeptide encoded by the sequence.

A "transcription factor" typically refers to a protein (or polypeptide) which affects the transcription, and accordingly the expression, of a specified gene. A transcription factor may refer to a single polypeptide transcription factor, one or more polypeptides acting sequentially or in concert, or a complex of polypeptides.

Typical "control elements" include, but are not limited to, transcription promoters, transcription enhancer elements, cis-acting transcription regulating elements (transcription regulators, e.g., a cis-acting element that affects the transcription of a gene, for example, a region of a promoter with which a transcription factor interacts to induce or repress expression of a gene), transcription initiation signals (e.g., TATA box), basal promoters, transcription termination signals, as well as polyadenylation sequences (located 3' to the translation stop codon), sequences for optimization of initiation of translation (located 5' to the coding sequence), translation enhancing sequences, and translation termination sequences. Transcription promoters can include, for example, inducible promoters (where expression of a polynucleotide sequence operably linked to the promoter is induced by an analyte, cofactor, regulatory protein, etc.), repressible promoters (where expression of a polynucleotide sequence operably linked to the promoter is induced by an analyte, cofactor, regulatory protein, etc.), and constitutive promoters.

"Expression enhancing sequences," also referred to as "enhancer sequences" or "enhancers," typically refer to control elements that improve transcription or translation of a polynucleotide relative to the expression level in the absence of such control elements (for example, promoters, promoter enhancers, enhancer elements, and translational enhancers (e.g., Shine and Delagarno sequences)).

The term "modulation" refers to both inhibition, including partial inhibition, as well as stimulation. Thus, for example, a compound that modulates expression of a reporter sequence may either inhibit that expression, either partially or completely, or stimulate expression of the sequence.

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well known in the art and include, for example, disruption of the cell containing the polynucleotide with a chaotropic agent and separation of the polynucleotide(s) and proteins by ion-exchange chromatography, affinity chromatography and sedimentation according to density.

A "heterologous sequence" typically refers to either (i) a nucleic acid sequence that is not normally found in the cell or organism of interest, or (ii) a nucleic acid sequence introduced at a genomic site wherein the nucleic acid sequence does not normally occur in nature at that site. For example, a DNA sequence encoding a polypeptide can be obtained from yeast and introduced into a bacterial cell. In this case the yeast DNA sequence is "heterologous" to the native DNA of the bacterial cell. Alternatively, a promoter sequence, for example, from a Tie2 gene can be introduced into the genomic location of a fosB gene. In this case the Tie2 promoter sequence is "heterologous" to the native fosB genomic sequence.

A "polypeptide" is used in it broadest sense to refer to a compound of two or more subunit amino acids, amino acid analogs, or other peptidomimetics. The subunits may be linked by peptide bonds or by other bonds, for example ester, ether, etc. The term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is typically called a polypeptide or a protein.

"Operably linked" refers to an arrangement of elements wherein the components so described are configured so as to perform their usual function. Thus, a given promoter that is operably linked to a coding sequence (e.g., a reporter expression cassette) is capable of effecting the expression of the coding sequence when the proper enzymes are present. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

"Recombinant" describes a nucleic acid molecule means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used interchange-ably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

An "isolated polynucleotide" molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482–489 (1981). This algorithm can be applied to amino acid sequences by using the scoring matrix developed by Dayhoff, *Atlas of Protein Sequences and Structure*, M. O. Dayhoff ed., 5 suppl. 3:353–358, National Biomedical Research Foundation, Washington, D.C., USA, and normalized by Gribskov, *Nucl. Acids Res.* 14(6):6745–6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR.

One of skill in the art can readily determine the proper search parameters to use for a given sequence in the above programs. For example, the search parameters may vary based on the size of the sequence in question. Thus, for example, a representative embodiment of the present invention would include an isolated polynucleotide comprising X contiguous nucleotides, wherein (i) the X contiguous nucleotides have at least about 50% identity to Y contiguous nucleotides derived from any of the sequences described herein, (ii) X equals Y, and (iii) X is equal to from 6 up to the number of nucleotides present in a selected full-length sequence as described herein (e.g., see the Examples, Figures, Sequence Listing and claims), including all integer values falling within the above-described ranges. A "fragment" of a polynucleotide refers to any length polynucleotide molecule derived from a larger polynucleotide described herein (i.e., Y contiguous nucleotides, where X=Y as just described). Exemplary fragment lengths include, but are not limited to, at least about 6 contiguous nucleotides, at least about 50 contiguous nucleotides, about 100 contiguous nucleotides, about 250 contiguous nucleotides, about 500 contiguous nucleotides, or at least about 1000 contiguous nucleotides or more, wherein such contiguous nucleotides are derived from a larger sequence of contiguous nucleotides.

The purified polynucleotides and polynucleotides used in construction of expression cassettes of the present invention include the sequences disclosed herein as well as related polynucleotide sequences having sequence identity of approximately 80% to 100% and integer values therebetween. Typically the percent identities between the sequences disclosed herein and the claimed sequences are at least about 80–85%, preferably at least about 90–92%, more preferably at least about 95%, and most preferably at least about 98% sequence identity (including all integer values falling within these described ranges). These percent identities are, for example, relative to the claimed sequences, or other sequences of the present invention, when the sequences of the present invention are used as the query sequence.

Alternatively, the degree of sequence similarity between polynucleotides can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80–85%, preferably 85–90%, more preferably 90–95%, and most preferably 98–100% sequence identity to the reference sequence over a defined length of the molecules, as determined using the methods above. Substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10–14 nucleotides in length having at least approximately 70% sequence identity with the sequence of the selected nucleic acid probe. Stringent hybridization conditions typically allow detection of target nucleic acid sequences of at least about 10–14 nucleotides in length having a sequence identity of greater than about 90–95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

"Nucleic acid expression vector" or "expression cassette" refers to an assembly that is capable of directing the expression of a sequence or gene of interest. The nucleic acid expression vector includes a promoter that is operably linked to the sequences or gene(s) of interest. Other control elements may be present as well. Expression cassettes described herein may be contained within a plasmid construct. In addition to the components of the expression cassette, the plasmid construct may also include a bacterial origin of replication, one or more selectable markers, a signal which allows the plasmid construct to exist as single-stranded DNA (e.g., a M13 origin of replication), a multiple cloning site, and a "mammalian" origin of replication (e.g., a SV40 or adenovirus origin of replication).

An "expression cassette" comprises any nucleic acid construct capable of directing the expression of a gene/coding sequence of interest. Such cassettes can be constructed into a "vector," "vector construct," "expression vector," or "gene transfer vector," in order to transfer the expression cassette into target cells. Thus, the term includes cloning and expression vehicles, as well as viral vectors.

A variety of "reporter genes" also referred to as "reporter sequences" and "marker sequences," i.e., genes or sequences the expression of which indicates the expression of polynucleotide sequences of interest to which the reporter gene or sequence is operably linked. Preferred are those reporter sequences that produce a protein product that is easily measured, preferably in a routine assay. Suitable reporter genes include, but are not limited to chloramphenicol acetyl transferase (CAT), light generating proteins (e.g., luc-encoded, lux-encoded, fluorescent proteins), and beta-galactosidase. Convenient assays include, but are not limited to calorimetric, fluorimetric and enzymatic assays. In one aspect, reporter genes may be employed that are expressed within the cell and whose extracellular products are directly measured in the intracellular medium, or in an extract of the intracellular medium of a cultured cell line. This provides advantages over using a reporter gene whose product is secreted, since the rate and efficiency of the secretion introduces additional variables that may complicate interpretation of the assay. In a preferred embodiment, the reporter gene is a light generating protein. When using the light generating reporter proteins described herein, expression can be evaluated accurately and non-invasively as described above (see, for example, Contag, P. R., et al., (1998) Nature Med. 4:245–7; Contag, C. H., et al., (1997) Photochem Photobiol. 66:523–31; Contag, C. H., et al., (1995) Mol Microbiol. 18:593–603).

A "light generating protein" or "light-emitting protein" is a bioluminescent or fluorescent protein capable of producing light typically in the range of 200 nm to 1100 nm, preferably in the visible spectrum (i.e., between approximately 350 nm and 800 nm). Bioluminescent proteins produce light through a chemical reaction (typically requiring a substrate, energy source, and oxygen). Fluorescent proteins produce light through the absorption and re-emission of radiation (such as with green fluorescent protein). Examples of bioluminescent proteins include, but are not limited to, the following: "luciferase," unless stated otherwise, includes procaryotic (e.g., bacterial lux-encoded) and eucaryotic (e.g., firefly luc-encoded) luciferases, as well as variants possessing varied or altered optical properties, such as luciferases that produce different colors of light (e.g., Kajiyama, N., and Nakano, E., *Protein Engineering* 4(6):691–693 (1991)); and "photoproteins," for example, calcium activated photoproteins (e.g., Lewis, J. C., et al., Fresenius *J. Anal. Chem.* 366(6–7):760–768 (2000)). Examples of fluorescent proteins include, but are not limited to, green, yellow, cyan, blue, and red fluorescent proteins (e.g., Hadjantonakis, A. K., et al., *Histochem. Cell Biol.* 115(1):49–58 (2001)).

"Bioluminescent protein substrate" describes a substrate of a light-generating protein, e.g., luciferase enzyme, that generates an energetically decayed substrate (e.g., luciferin) and a photon of light typically with the addition of an energy source, such as ATP or FMNH2, and oxygen. Examples of such substrates include, but are not limited to, decanal in the bacterial lux system, 4,5-dihydro-2-(6-hydroxy-2-benzothiazolyl)-4-thiazolecarboxylic acid (or simply called luciferin) in the Firefly luciferase (luc) system, "panal" in the bioluminescent fungus *Panellus stipticus* system (Tetrahedron 44:1597–1602, 1988) and N-iso-valeryl-3-aminopropanol in the earth worm *Diplocardia longa* system (Biochem. 15:1001–1004, 1976). In some systems, as described herein, aldehyde can be used as a substrate for the light-generating protein.

"Light" is defined herein, unless stated otherwise, as electromagnetic radiation having a wavelength of between about 200 nm (e.g., for UV-C) and about 1100 nm (e.g., infrared). The wavelength of visible light ranges between approximately 350 nm to approximately 800 nm (i.e., between about 3,500 angstroms and about 8,000 angstroms).

"Animal" typically refers to a non-human animal, including, without limitation, farm animals such as cattle, sheep, pigs, goats and horses; domestic mammals such as dogs and cats; laboratory animals including ferrets, hares and rabbits, rodents, such as mice, rats, hamsters, gerbils, and guinea pigs; non-human primates, including chimpanzees. The term "animal" may also include, without limitation; birds, including domestic, wild and game birds such as chickens, turkeys and other gallinaceous birds, ducks, geese, and the like, as well as amphibians, fish, insects, reptiles, etc. The term does not denote a particular age. Thus, adult, embryonic, fetal, and newborn individuals are intended to be covered.

A "transgenic animal" refers to a genetically engineered animal or offspring of genetically engineered animals. A transgenic animal usually contains material from at least one unrelated organism, such as from a virus, microorganism, plant, or other animal. The term "chimeric animal" is used to refer to animals in which the heterologous gene is found, or in which the heterologous gene is expressed in some but not all cells of the animal.

"Analyte" refers to any compound or substance whose effects (e.g., induction or repression of a specific promoter) can be evaluated using the test animals and methods of the present invention. Such analytes include, but are not limited to, chemical compounds, pharmaceutical compounds, polypeptides, peptides, polynucleotides, and polynucleotide analogs. Many organizations (e.g., the National Institutes of Health, pharmaceutical and chemical corporations) have large libraries of chemical or biological compounds from natural or synthetic processes, or fermentation broths or extracts. Such compounds/analytes can be employed in the practice of the present invention.

The term "positive selection marker" refers to a gene encoding a product that enables only the cells that carry the gene to survive and/or grow under certain conditions. For example, plant and animal cells that express the introduced neomycin resistance (Neo$^r$) gene are resistant to the compound G418. Cells that do not carry the Neo$^r$ gene marker are killed by G418. Other positive selection markers will be known to those of skill in the art. Typically, positive selection markers encode products that can be readily assayed. Thus, positive selection markers can be used to determine whether a particular DNA construct has been introduced into a cell, organ or tissue.

"Negative selection marker" refers to gene encoding a product that can be used to selectively kill and/or inhibit growth of cells under certain conditions. Non-limiting examples of negative selection inserts include a herpes simplex virus (HSV)-thymidine kinase (TK) gene. Cells containing an active HSV-TK gene are incapable of growing in the presence of gangcylovir or similar agents. Thus, depending on the substrate, some gene products can act as either positive or negative selection markers.

The term "homologous recombination" refers to the exchange of DNA fragments between two DNA molecules or chromatids at the site of essentially identical nucleotide sequences. It is understood that substantially homologous sequences can accommodate insertions, deletions, and substitutions in the nucleotide sequence. Thus, linear sequences of nucleotides can be essentially identical even if some of the nucleotide residues do not precisely correspond or align (see, above).

A "knock-out" mutation refers to partial or complete loss of expression of at least a portion the target gene. Examples of knock-out mutations include, but are not limited to, gene-replacement by heterologous sequences, gene disruption by heterologous sequences, and deletion of essential elements of the gene (e.g., promoter region, portions of a coding sequence). A "knock-out" mutation is typically identified by the phenotype generated by the mutation.

A "gene" as used in the context of the present invention is a sequence of nucleotides in a genetic nucleic acid (chromosome, plasmid, etc.) with which a genetic function is associated. A gene is a hereditary unit, for example of an organism, comprising a polynucleotide sequence (e.g., a DNA sequence for mammals) that occupies a specific physical location (a "locus", "gene locus" or "genetic locus") within the genome of an organism. A gene can encode an expressed product, such as a polypeptide or a polynucleotide (e.g., tRNA). Alternatively, a gene may define a genomic location for a particular event/function, such as the binding of proteins and/or nucleic acids (e.g., phage attachment sites), wherein the gene does not encode an expressed product. Typically, a gene includes coding sequences, such as, polypeptide encoding sequences, and non-coding sequences, such as, transcription control elements (e.g., promoter sequences), poly-adenylation sequences, transcriptional regulatory sequences (e.g., enhancer sequences). Many eucaryotic genes have "exons" (coding sequences) interrupted by "introns" (non-coding sequences). In certain cases, a gene may share sequences with another gene(s) (e.g., overlapping genes).

The "native sequence" or "wild-type sequence" of a gene is the polynucleotide sequence that comprises the genetic locus corresponding to the gene, e.g., all regulatory and open-reading frame coding sequences required for expression of a completely functional gene product as they are present in the wild-type genome of an organism. The native sequence of a gene can include, for example, transcriptional promoter sequences, translation enhancing sequences, introns, exons, and poly-A processing signal sites. It is noted that in the general population, wild-type genes may include multiple prevalent versions that contain alterations in sequence relative to each other and yet do not cause a discernible pathological effect. These variations are designated "polymorphisms" or "allelic variations."

By "replacement sequence" is meant a polynucleotide sequence that is substituted for at least a portion of the native or wild-type sequence of a gene.

"Linear vector" or "linearized vector," is a vector having two ends. For example, circular vectors, such as plasmids, can be linearized by digestion with a restriction endonuclease that cuts at a single site in the plasmid. Preferably, the expression vectors described herein are linearized such that the ends are not within the sequences of interest.

Before describing the present invention in detail, it is to be understood that this invention is not limited to particular formulations or method parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

2. Modes of Carrying out the Invention

Throughout this application, various publications, patents, and published patent applications are referred to by an identifying citation. The disclosures of these publications, patents, and published patent specifications referenced in this application are hereby incorporated by reference into the present disclosure to more fully describe the state of the art to which this invention pertains.

As used in this specification and the appended claims, the singular forms "a," "an" and "the" include plural references unless the content clearly dictates otherwise. Thus, for example, reference to "an expression construct" includes a mixture of two or more such agents.

2.1 General Overview

In one aspect, the present invention relates to novel transcription control elements derived from the mouse eosinophil peroxidase (EPX) gene locus, expression cassettes which include these control elements, vector constructs, cells and transgenic animals containing the expression cassettes, and methods of using the cells and transgenic animals containing the expression cassettes, for example, as modeling, screening and/or test systems. Methods of using the control elements, expression cassettes, cells, and transgenic animals of the present invention include, but are not limited to, studies involving host immunity, allergic reactions and drug metabolism, and methods for screening for compounds which affect expression of the mouse eosinophil peroxidase (EPX) gene. Exemplary transcription control elements useful in the practice of the present invention include those derived from mouse eosinophil peroxidase (EPX) gene locus.

In one embodiment, the present invention relates to (1) novel transcription control elements (e.g., promoters) derived from the mouse eosinophil peroxidase (EPX) gene locus; (2) expression cassettes comprising such transcription control elements operatively linked to genes encoding a gene product, such as, a reporter, a protein, polypeptide, hormone, ribozyme, or antisense RNA, (3) recombinant cells comprising such expression cassettes, (4) methods of screening using such cells (e.g., screening for the effects of a compound or compounds on expression of the mouse eosinophil peroxidase (EPX) gene, (5) animals (e.g., transgenic or transiently transfected) comprising the aforementioned novel transcription control elements, expression cassettes and vector constructs, (6) methods of monitoring the effect of a compound or compounds on expression of the mouse eosinophil peroxidase (EPX) using such animals, and (7) methods of evaluating pathophysiology involving the mouse eosinophil peroxidase (EPX) using such animals.

Non-invasive imaging and/or detecting of light-emitting conjugates in mammalian subjects was described in U.S. Pat. Nos. 5,650,135, and 6,217,847, by Contag, et al., issued 22 Jul. 1997, and Apr. 17, 2001, respectively, and herein incorporated by reference. This imaging technology can be used in the practice of the present invention in view of the teachings of the present specification. In the imaging method, the conjugates contain a biocompatible entity and a light-generating moiety. Biocompatible entities include, but are not limited to, small molecules such as cyclic organic molecules; macromolecules such as proteins; microorganisms such as viruses, bacteria, yeast and fungi; eucaryotic cells; all types of pathogens and pathogenic substances; and particles such as beads and liposomes. In another aspect, biocompatible entities may be all or some of the cells that constitute the mammalian subject being imaged, for example, cells carrying the expression cassettes of the present invention expressing a reporter sequence.

Light-emitting capability is conferred on the biocompatible entities by the conjugation of a light-generating moiety. Such moieties include fluorescent molecules, fluorescent proteins, enzymatic reactions which give off photons, and luminescent substances, such as bioluminescent proteins. In the context of the present invention, light emitting capability is typically conferred on target cells by having at least one copy of a light-generating protein, e.g., a luciferase, present. In preferred embodiments, luciferase is operably linked to appropriate control elements that can facilitate expression of a polypeptide having luciferase activity. Substrates of luciferase can be endogenous to the cell or applied to the cell or system (e.g., injection into a transgenic mouse, having cells carrying a luciferase construct, of a suitable substrate for the luciferase, for example, luciferin). The conjugation may involve a chemical coupling step, genetic engineering of a fusion protein, or the transformation of a cell, microorganism or animal to express a light-generating protein.

Thus, in one aspect, the present invention relates to animal test systems and methods for studies of an analyte of interest for their effects on expression of the mouse eosinophil peroxidase (EPX) gene. In the practice of the present invention, transgenic mammals (e.g., rodents, including, but not limited to, mice or rats) are constructed where control elements, for example, a promoter or transcriptional regulatory sequence from the mouse eosinophil peroxidase (EPX) gene locus are operably linked to reporter gene coding sequences (for example, luciferase). An appropriate substrate for the reporter gene product is administered to the animal in addition to an analyte of interest. The order of administration of these two substances can be empirically determined for each analyte of interest. Induction of expression mediated by any of the control elements is then evaluated by non-invasive imaging methods using the whole animal.

Thus, in one aspect of the present invention, animals described herein can be used to evaluate the in vivo effects of therapeutic substances on the expression of the mouse eosinophil peroxidase (EPX) gene. As described above, eosinophils play a protective role in host immunity to parasitic worm infections and, detrimentally, are involved in the pathophysiology of asthma and other allergic diseases. Eosinophils are prominent in airway inflammation. Eosinophils are involved in disease like asthma, chronic eosinophilic pneumonia, Churg-Strauss Syndrome, Hypereosinophilic syndrome, allergic rhinitis, atopic dermatitis. The present invention allows marking eosinophils in vivo. Thus an eosinophil migration model can be established in animals, e.g., transgenic rodents, so that the effects of drug candidates can be tested efficiently. The eosinophil peroxidase (EPX) gene is known to be exclusively expressed in eosinophils. Accordingly, linking transcription control elements, associated with the expression of this gene, to a reporter sequence allows the specific tagging (or marking) of eosinophils in vivo.

2.2 Promoters

The expression cassettes, vectors, cells and transgenic animals described herein contain a sequence encoding a detectable gene product, e.g., a luciferase gene, operably linked to a transcription control element, e.g., a promoter. The promoter may be from the same species as the transgenic animal (e.g., mouse promoter used in construct to make transgenic mouse) or from a different species (e.g., mouse promoter used in construct to make transgenic rat). In one embodiment of the present invention, the promoter is derived from the mouse eosinophil peroxidase (EPX) gene. Based on the teachings of the present invention, eosinophil peroxidase (EPX) genes may be isolated from other sources as well, e.g., human, rat, or guinea pig. Thus, when a drug is administered to a transgenic animal carrying a vector construct of the present invention, the promoter may be induced or repressed and expression of the reporter, e.g., luciferase, can then be monitored in vivo.

Exemplary transcription control elements (e.g., promoters) for use in the present invention include, but are not limited to, promoters derived from eosinophil peroxidase (EPX) genes. Exemplified herein are novel transcription control elements derived from the genomic locus of the mouse eosinophil peroxidase (EPX) gene.

As one of skill in the art will appreciate in view of the teachings of the present specification, transcription control element sequences can be derived and isolated from, e.g., genomic sequences, using method known in the art in view of the teachings herein. For example, the transcription control element sequences of the mouse eosinophil peroxidase (EPX) gene were isolated and sequenced as described in Example 1 below.

Another exemplary method of isolating promoter sequences employs a Genome Walker® kit, commercially available from Clontech (Palo Alto, Calif.), and described on page 27 of the 1997–1998 Clontech catalog.

The subject nucleic acids of the present invention (e.g., as described in Example 1) find a wide variety of applications including use as hybridization probes, PCR primers, expression cassettes useful for compound screening, detecting the presence of the mouse eosinophil peroxidase (EPX) gene or variants thereof, detecting the presence of gene transcripts, detecting or amplifying nucleic acids encoding additional eosinophil peroxidase (EPX) gene promoter sequences or homologues thereof (as well as, structural analogs), and in a variety of screening assays.

A wide variety of assays for transcriptional expression can be used based on the teaching of the present specification, including, but not limited to, cell-based transcription assays, screening in vivo in transgenic animals, and promoter-protein binding assays. For example, the disclosed luciferase reporter constructs are used to transfect eosinophil cells for cell-based transcription assays. For example, eosinophil cells are plated onto microtiter plates and used to screen libraries of candidate agents for compounds which modulate the transcriptional regulation of the eosinophil peroxidase (EPX) gene promoter, as monitored by luciferase expression.

Experiments performed in support of the present invention involve the isolation and sequencing of a transcriptional control elements of a mouse eosinophil peroxidase (EPX) gene, generation of transgenic mice comprising these transcriptional control elements operatively linked to sequences encoding a light-generating protein (e.g., luciferase), and the utilization of these transgenic mice to establish an eosinophil migration model. The mouse eosinophil peroxidase (EPX) gene promoter sequences have not been previously characterized. Identification of the sequence of the transcriptional control regions of the mouse eosinophil peroxidase (EPX) gene will facilitate the analysis of eosinophil peroxidase (EPX) gene expression regulation studies in vitro and in vivo. An animal, e.g., mouse, eosinophil migration model will greatly enhance the process of validating compounds (or analytes) that can be used in the management of eosinophil-related disease states, that is, disease states where eosinophils serve as a marker.

As noted above, the present invention relates to a recombinant nucleic acid molecule comprising transcription control elements derived from a mouse eosinophil peroxidase (EPX) gene locus. Isolation and characterization of these sequences is described below in Example 1. In particular, recombinant nucleic acid molecules comprising SEQ ID NO:1 and SEQ ID NO:2, as well as fragments thereof, are described. The fragments have approximately 80% to 100%, and integer values therebetween, sequence identity to sequences disclosed, at least 80–85%, preferably 85–90%, more preferably 90–95%, and most preferably 98–100% sequence identity to the reference sequence (i.e., the sequences of the present invention). The present invention may also include a nucleic acid sequence substantially complementary to said polynucleotide sequences, or fragments thereof, as well as, a nucleic acid sequence that specifically hybridizes to said polynucleotide sequences or fragments thereof.

The invention includes further transcription control element sequences (e.g., promoter sequences) identified based on the teachings of the present specification (including, but not limited to, sequence information and isolation methods, e.g., Example 1).

The nucleic acid molecules of this invention are useful for producing transfected cells and transgenic animals that are themselves useful in a variety of applications, for example, for screening for compounds that affect transcription mediated by the mouse eosinophil peroxidase (EPX) gene transcriptional control elements.

Those skilled in the art can practice the invention by following the guidance of the specification supplemented with standard procedures of molecular biology for the isolation and characterization of mouse eosinophil peroxidase (EPX) gene locus transcription control elements, their transfection into host cells, and expression of heterologous DNA operably linked to said EPX promoters. For example, DNA is commonly transferred or introduced into recipient mammal cells by calcium phosphate-mediated gene transfer, electroporation, lipofection, viral infection, and the like. General methods and vectors for gene transfer and expression may be found, for example, in M. Kriegler, Gene Transfer and Expression: A Laboratory Manual, Stockton Press (1990). Direct gene transfer to cells in vivo can be achieved, for example, by the use of modified viral vectors, including, but not limited to, retroviruses, adenoviruses, adeno-associated viruses and herpes viruses, liposomes, and direct injection of DNA into certain cell types. In this manner, recombinant expression vectors and recombinant cells containing the novel EPX transcription control elements of the present invention operably linked to a desired heterologous gene can be delivered to specific target cells in vivo. See, e.g., Wilson, Nature, 365: 691–692 (1993); Plautz et al, Annals NY Acad. Sci., 716: 144–153 (1994); Farhood et al, Annals NY Acad. Sci., 716: 23–34 (1994) and Hyde et al Nature, 362: 250–255 (1993). Furthermore, cells may be transformed ex vivo and introduced directly at localized sites by injection, e.g., intra-articular, intracutaneous, intramuscular and the like.

Cloning and characterization of the EPX-locus-derived transcription control elements are described in Example 1, below.

Activity of the transcription control element sequences comprising the expression cassettes and vectors of the present invention may be monitored by detecting and/or quantifying the protein products encoded by the reporter sequences operably linked to those promoters. The particular method used to monitor promoter activity depends on the reporter sequence employed, and may include, for example, enzymatic assay methods, as well as, in the case of reporter sequences which encode light-generating proteins, in vitro or in vivo bioluminescent imaging.

Monitoring promoter activity in turn enables one to monitor the biological processes with which that promoter is associated. It may further be employed in methods of screening analytes which modulate those processes at the promoter level (see below).

2.3 Expression Cassettes and Vectors

The expression cassettes described herein may typically include the following components: (1) a polynucleotide encoding a reporter gene, such as a sequence encoding a light generating protein, (2) a transcription control element operably linked to the reporter gene sequence, wherein the control element is heterologous to the coding sequences of the light generating protein (e.g., the novel EPX sequences of the present invention). Transcription control elements derived from the sequences provided herein may be associated with, for example, a basal transcription promoter to confer regulation provided by such control elements on such a basal transcription promoter. Exemplary expression constructs are described in Example 1.

The present invention also includes providing such expression cassettes in vectors, comprising, for example, a suitable vector backbone and optionally a sequence encoding a selection marker e.g., a positive or negative selection marker. Suitable vector backbones generally include an F1 origin of replication; a colE1 plasmid-derived origin of replication; polyadenylation sequence(s); sequences encoding antibiotic resistance (e.g., ampicillin resistance) and other regulatory or control elements. Non-limiting examples of appropriate backbones include: pBluescriptSK (Stratagene, La Jolla, Calif.); pBluescriptKS (Stratagene, La Jolla, Calif.) and other commercially available vectors.

A variety of reporter genes may be used in the practice of the present invention. Preferred are those that produce a protein product which is easily measured in a routine assay. Suitable reporter genes include, but are not limited to chloramphenicol acetyl transferase (CAT), light generating proteins (e.g., luciferase), and beta-galactosidase. Convenient assays include, but are not limited to calorimetric, fluorimetric and enzymatic assays. In one aspect, reporter genes may be employed that are expressed within the cell and whose extracellular products are directly measured in the intracellular medium, or in an extract of the intracellular medium of a cultured cell line. This provides advantages over using a reporter gene whose product is secreted, since the rate and efficiency of the secretion introduces additional variables that may complicate interpretation of the assay. In a preferred embodiment, the reporter gene is a light generating protein. When using the light generating reporter proteins described herein, expression can be evaluated accurately and non-invasively as described above (see, for example, Contag, P. R., et al., (1998) Nature Med. 4:245–7; Contag, C. H., et al., (1997) Photochem Photobiol. 66:523–31; Contag, C. H., et al., (1995) Mol Microbiol. 18:593–603).

In one aspect of the invention, the light generating is luciferase. Luciferase coding sequences useful in the practice of the present invention include sequences obtained from lux genes (procaryotic genes encoding a luciferase activity) and luc genes (eucaryotic genes encoding a luciferase activity). A variety of luciferase encoding genes have been identified including, but not limited to, the following: B. A. Sherf and K. V. Wood, U.S. Pat. No. 5,670,356, issued 23 Sep. 1997; Kazami, J., et al., U.S. Pat. No. 5,604,123, issued 18 Feb. 1997; S. Zenno, et al, U.S. Pat. No. 5,618,722; K. V. Wood, U.S. Pat. No. 5,650,289, issued 22 Jul. 1997; K. V. Wood, U.S. Pat. No. 5,641,641, issued 24 Jun. 1997; N. Kajiyama and E. Nakano, U.S. Pat. No. 5,229,285, issued 20 Jul. 1993; M. J. Cormier and W. W. Lorenz, U.S. Pat. No. 5,292,658, issued 8 Mar. 1994; M. J. Cormier and W. W. Lorenz, U.S. Pat. No. 5,418,155, issued 23 May 1995; de Wet, J. R., et al, *Molec. Cell. Biol.* 7:725–737, 1987; Tatsumi, H. N., et al, *Biochim. Biophys. Acta* 1131:161–165, 1992; and Wood, K. V., et al, *Science* 244:700–702, 1989; all herein incorporated by reference. Another group of bioluminescent proteins includes light-generating proteins of the aequorin family (Prasher, D. C., et al., Biochem. 26:1326–1332 (1987)). Luciferases, as well as aequorin-like molecules, require a source of energy, such as ATP, NAD(P)H, and the like, and a substrate, such as luciferin or coelentrizine and oxygen.

Wild-type firefly luciferases typically have emission maxima at about 550 nm. Numerous variants with distinct emission maxima have also been studied. For example, Kajiyama and Nakano (*Protein Eng.* 4(6):691–693, 1991; U.S. Pat. No. 5,330,906, issued 19 Jul. 1994, herein incorporated by reference) teach five variant firefly luciferases generated by single amino acid changes to the *Luciola cruciata* luciferase coding sequence. The variants have emission peaks of 558 nm, 595 nm, 607 nm, 609 nm and 612 nm. A yellow-green luciferase with an emission peak of about 540 nm is commercially available from Promega, Madison, Wis. under the name pGL3. A red luciferase with an emission peak of about 610 nm is described, for example, in Contag et al. (1998) *Nat. Med.* 4:245–247 and Kajiyama et al. (1991) *Port. Eng.* 4:691–693. The coding sequence of a luciferase derived from *Renilla muelleri* has also been described (mRNA, GENBANK Accession No. AY015988, protein Accession AAG54094).

In another aspect of the present invention, the light-generating protein is a fluorescent protein, for example, blue, cyan, green, yellow, and red fluorescent proteins.

Several light-generating protein coding sequences are commercially available, including, but not limited to, the following. Clontech (Palo Alto, Calif.) provides coding sequences for luciferase and a variety of fluorescent proteins, including, blue, cyan, green, yellow, and red fluorescent proteins. Enhanced green fluorescent protein (EGFP) variants are well expressed in mammalian systems and tend to exhibit brighter fluorescence than wild-type GFP. Enhanced fluorescent proteins include enhanced green fluorescent protein (EGFP), enhanced cyan fluorescent protein (ECFP), and enhanced yellow fluorescent protein (EYFP). Further, Clontech provides destabilized enhanced fluorescent proteins (dEFP) variants that feature rapid turn over rates. The shorter half life of the dEFP variants makes them useful in kinetic studies and as quantitative reporters. DsRed coding sequences are available from Clontech.

DsRed is a red fluorescent protein useful in expression studies. Further, Fradkov, A. F., et. al., described a novel fluorescent protein from Discosoma coral and its mutants which possesses a unique far-red fluorescence (FEBS Lett. 479 (3), 127–130 (2000)) (mRNA sequence, GENBANK Accession No. AF272711, protein sequence, GENBANK Accession No. AAG16224). Promega (Madison, Wis.) also provides coding sequences for fire fly luciferase (for example, as contained in the pGL3 vectors). Further, coding sequences for a number of fluorescent proteins are available from GENBANK, for example, accession numbers AY015995, AF322221, AF080431, AF292560, AF292559, AF292558, AF292557, AF139645, U47298, U47297, AY015988, AY015994, and AF292556.

Modified lux coding sequences have also been described, e.g., WO 01/18195, published 15 Mar. 2001, Xenogen Corporation. In addition, further light generating systems may be employed, for example, when evaluating expression in cells. Such systems include, but are not limited to, Luminescent beta-galactosidase Genetic Reporter System (Clontech).

Positive selection markers include any gene which a product that can be readily assayed. Examples include, but are not limited to, an HPRT gene (Littlefield, J. W., Science 145:709–710 (1964), herein incorporated by reference), a xanthine-guanine phosphoribosyltransferase (GPT) gene, or an adenosine phosphoribosyltransferase (APRT) gene (Sambrook et al., supra), a thymidine kinase gene (i.e. "TK") and especially the TK gene of the herpes simplex virus (Giphart-Gassler, M. et al., Mutat. Res. 214:223–232 (1989) herein incorporated by reference), a nptII gene (Thomas, K. R. et al., Cell 51:503–512 (1987); Mansour, S. L. et al., Nature 336:348–352 (1988), both references herein incorporated by reference), or other genes which confer resistance to amino acid or nucleoside analogues, or antibiotics, etc., for example, gene sequences which encode enzymes such as dihydrofolate reductase (DHFR) enzyme, adenosine deaminase (ADA), asparagine synthetase (AS), hygromycin B phosphotransferase, or a CAD enzyme (carbamyl phosphate synthetase, aspartate transcarbamylase, and dihydroorotase). Addition of the appropriate substrate of the positive selection marker can be used to determine if the product of the positive selection marker is expressed, for example cells which do not express the positive selection marker nptII, are killed when exposed to the substrate G418 (Gibco BRL Life Technology, Gaithersburg, Md.).

The vector typically contains insertion sites for inserting polynucleotide sequences of interest, e.g., the novel EPX sequences of the present invention. These insertion sites are preferably included such that there are two sites, one site on either side of the sequences encoding the positive selection marker, luciferase and the promoter. Insertion sites are, for example, restriction endonuclease recognition sites, and can, for example, represent unique restriction sites. In this way, the vector can be digested with the appropriate enzymes and the sequences of interest ligated into the vector.

Optionally, the vector construct can contain a polynucleotide encoding a negative selection marker. Suitable negative selection markers include, but are not limited to, HSV-tk (see, e.g., Majzoub et al. (1996) *New Engl. J. Med.* 334: 904–907 and U.S. Pat. No. 5,464,764), as well as genes encoding various toxins including the diphtheria toxin, the tetanus toxin, the cholera toxin and the pertussis toxin. A further negative selection marker gene is the hypoxanthine-guanine phosphoribosyl transferase (HPRT) gene for negative selection in 6-thioguanine.

The vectors described herein can be constructed utilizing methodologies known in the art of molecular biology (see, for example, Ausubel or Maniatis) in view of the teachings of the specification. As described above, the vector constructs containing the expression cassettes are assembled by inserting the desired components into a suitable vector backbone, for example: a vector comprising (1) polynucleotides encoding a reporter protein, such as a light-generating protein, e.g., a luciferase gene, operably linked to a transcription control element(s) of interest derived from the mouse eosinophil peroxidase (EPX) gene locus; (2) a sequence encoding a positive selection marker; and, optionally (3) a sequence encoding a negative selection marker. In addition, the vector construct contains insertion sites such that additional sequences of interest can be readily inserted to flank the sequence encoding positive selection marker and luciferase-encoding sequence.

A preferred method of obtaining polynucleotides, suitable regulatory sequences (e.g., promoters) is PCR. General procedures for PCR as taught in MacPherson et al., PCR: A PRACTICAL APPROACH, (IRL Press at Oxford University Press, (1991)). PCR conditions for each application reaction may be empirically determined. A number of parameters influence the success of a reaction. Among these parameters are annealing temperature and time, extension time, Mg2+ and ATP concentration, pH, and the relative concentration of primers, templates and deoxyribonucleotides. Exemplary primers are described below in the Examples. After amplification, the resulting fragments can be detected by agarose gel electrophoresis followed by visualization with ethidium bromide staining and ultraviolet illumination.

In one embodiment, PCR can be used to amplify fragments from genomic libraries. Many genomic libraries are commercially available. Alternatively, libraries can be produced by any method known in the art. Preferably, the organism(s) from which the DNA is has no discernible disease or phenotypic effects. This isolated DNA may be obtained from any cell source or body fluid (e.g., eosinophil cells, ES cells, liver, kidney, blood cells, buccal cells, cerviovaginal cells, epithelial cells from urine, fetal cells, or any cells present in tissue obtained by biopsy, urine, blood, cerebrospinal fluid (CSF), and tissue exudates at the site of infection or inflammation). DNA is extracted from the cells or body fluid using known methods of cell lysis and DNA purification. The purified DNA is then introduced into a suitable expression system, for example a lambda phage. Another method for obtaining polynucleotides, for example, short, random nucleotide sequences, is by enzymatic digestion.

Polynucleotides are inserted into vector backbones using methods known in the art. For example, insert and vector DNA can be contacted, under suitable conditions, with a restriction enzyme to create complementary or blunt ends on each molecule that can pair with each other and be joined with a ligase. Alternatively, synthetic nucleic acid linkers can be ligated to the termini of a polynucleotide. These synthetic linkers can contain nucleic acid sequences that correspond to a particular restriction site in the vector DNA. Other means are known and, in view of the teachings herein, can be used.

The vector backbone may comprise components functional in more than one selected organism in order to provide a shuttle vector, for example, a bacterial origin of replication and a eucaryotic promoter. Alternately, the vector backbone may comprise an integrating vector, i.e., a vector that is used for random or site-directed integration into a target genome.

The final constructs can be used immediately (e.g., for introduction into ES cells or for liver-push assays), or stored frozen (e.g., at −20° C.) until use. In some embodiments, the constructs are linearized prior to use, for example by digestion with suitable restriction endonucleases.

2.4 Transgenic Animals

The expression cassettes of the present invention may be introduced into the genome of an animal in order to produce transgenic, non-human animals for purposes of practicing the methods of the present invention. In a preferred embodiment of the present invention, the transgenic non-human, animal may be a rodent (e.g., rodents, including, but not limited to, mice, rats, hamsters, gerbils, and guinea pigs). When a light-generating protein is used as a reporter, imaging is typically carried out using an intact, living, non-human transgenic animal, for example, a living, transgenic rodent (e.g., a mouse or rat). A variety of transformation techniques are well known in the art. Those methods include the following.

(i) Direct microinjection into nuclei: Expression cassettes can be microinjected directly into animal cell nuclei using micropipettes to mechanically transfer the recombinant DNA. This method has the advantage of not exposing the DNA to cellular compartments other than the nucleus and of yielding stable recombinants at high frequency. See, Capecchi, M., Cell 22:479–488 (1980).

For example, the expression cassettes of the present invention may be microinjected into the early male pronucleus of a zygote as early as possible after the formation of the male pronucleus membrane, and prior to its being processed by the zygote female pronucleus. Thus, microinjection according to this method should be undertaken when the male and female pronuclei are well separated and both are located close to the cell membrane. See, e.g., U.S. Pat. No. 4,873,191 to Wagner, et al. (issued Oct. 10, 1989); and Richa, J., (2001) "Production of Transgenic Mice," Molecular Biotechnology, March 2001 vol. 17:261–8.

(ii) ES Cell Transfection: The DNA containing the expression cassettes of the present invention can also be introduced into embryonic stem ("ES") cells. ES cell clones which undergo homologous recombination with a targeting vector are identified, and ES cell-mouse chimeras are then produced. Homozygous animals are produced by mating of hemizygous chimera animals. Procedures are described in, e.g., Koller, B. H. and Smithies, O., (1992) "Altering genes in animals by gene targeting", Annual review of immunology 10:705–30.

(iii) Electroporation: The DNA containing the expression cassettes of the present invention can also be introduced into the animal cells by electroporation. In this technique, animal cells are electroporated in the presence of DNA containing the expression cassette. Electrical impulses of high field strength reversibly permeabilize biomembranes allowing the introduction of the DNA. The pores created during electroporation permit the uptake of macromolecules such as DNA. Procedures are described in, e.g., Potter, H., et al., Proc. Nat'l. Acad. Sci. U.S.A. 81:7161–7165 (1984); and Sambrook, ch. 16.

(iv) Calcium phosphate precipitation: The expression cassettes may also be transferred into cells by other methods of direct uptake, for example, using calcium phosphate. See, e.g., Graham, F., and A. Van der Eb, Virology 52:456–467 (1973); and Sambrook, ch. 16.

(v) Liposomes: Encapsulation of DNA within artificial membrane vesicles (liposomes) followed by fusion of the liposomes with the target cell membrane can also be used to introduce DNA into animal cells. See Mannino, R. and S. Gould-Fogerite, BioTechniques, 6:682 (1988).

(vi) Viral capsids: Viruses and empty viral capsids can also be used to incorporate DNA and transfer the DNA to animal cells. For example, DNA can be incorporated into empty polyoma viral capsids and then delivered to polyoma-susceptible cells. See, e.g., Slilaty, S. and H. Aposhian, Science 220:725 (1983).

(vii) Transfection using polybrene or DEAE-dextran: These techniques are described in Sambrook, ch. 16.

(viii) Protoplast fusion: Protoplast fusion typically involves the fusion of bacterial protoplasts carrying high numbers of a plasmid of interest with cultured animal cells, usually mediated by treatment with polyethylene glycol. Rassoulzadegan, M., et al., Nature, 295:257 (1982).

(ix) Ballistic penetration: Another method of introduction of nucleic acid segments is high velocity ballistic penetration by small particles with the nucleic acid either within the matrix of small beads or particles, or on the surface, Klein, et al., Nature, 327, 70–73, 1987.

Any technique that can be used to introduce DNA into the animal cells of choice can be employed (e.g., "Transgenic Animal Technology: A Laboratory Handbook," by Carl A. Pinkert, (Editor) First Edition, Academic Press; ISBN: 0125571658; "Manipulating the Mouse Embryo: A Laboratory Manual," Brigid Hogan, et al., ISBN: 0879693843, Publisher: Cold Spring Harbor Laboratory Press, Pub. Date: September 1999, Second Edition.). Electroporation has the advantage of ease and has been found to be broadly applicable, but a substantial fraction of the targeted cells may be killed during electroporation. Therefore, for sensitive cells or cells which are only obtainable in small numbers, microinjection directly into nuclei may be preferable. Also, where a high efficiency of DNA incorporation is especially important, such as transformation without the use of a selectable marker (as discussed above), direct microinjection into nuclei is an advantageous method because typically 5–25% of targeted cells will have stably incorporated the microinjected DNA. Retroviral vectors are also highly efficient but in some cases they are subject to other shortcomings, as described by Ellis, J., and A. Bernstein, Molec. Cell. Biol. 9:1621–1627 (1989). Where lower efficiency techniques are used, such as electroporation, calcium phosphate precipitation or liposome fusion, it is preferable to have a selectable marker in the expression cassette so that stable transformants can be readily selected, as discussed above.

In some situations, introduction of the heterologous DNA will itself result in a selectable phenotype, in which case the targeted cells can be screened directly for homologous recombination. For example, disrupting the gene hart results in resistance to 6-thioguanine. In many cases, however, the transformation will not result in such an easily selectable phenotype and, if a low efficiency transformation technique such as calcium phosphate precipitation is being used, it is preferable to include in the expression cassette a selectable marker such that the stable integration of the expression cassette in the genome will lead to a selectable phenotype. For example, if the introduced DNA contains a neo gene, then selection for integrants can be achieved by selecting cells able to grow on G418.

Transgenic animals prepared as above are useful for practicing the methods of the present invention. Operably linking a promoter of interest to a reporter sequence enables persons of skill in the art to monitor a wide variety of biological processes involving expression of the gene from which the promoter is derived. The transgenic animals of the present invention that comprise the expression cassettes of the present invention provide a means for skilled artisans to observe those processes as they occur in vivo, as well as to elucidate the mechanisms underlying those processes.

With respect to transgenic animals carrying expression cassettes that employ a light-generating protein as a reporter sequence, the monitoring of expression of luciferase reporter expression cassettes using non-invasive whole animal imaging has been described (Contag, C. et al, U.S. Pat. Nos. 5,650,135, and 6,217,847, issued 22 Jul. 1997, and Apr. 17, 2001, respectively, herein incorporated by reference in their entireties; Contag, P., et al, Nature Medicine 4 (2):245–247, 1998; Contag, C., et al, OSA TOPS on Biomedical Optical Spectroscopy and Diagnostics 3:220–224, 1996; Contag, C. H., et al, Photochemistry and Photobiology 66 (4):523–531, 1997; Contag, C. H., et al, Molecular Microbiology 18 (4):593–603, 1995). Such imaging typically uses at least one photo detector device element, for example, a charge-coupled device (CCD) camera.

Thus, in one exemplary embodiment, transgenic mice carrying expression cassettes comprising control elements derived from the mouse eosinophil peroxidase (EPX) gene locus operably linked to a luciferase-encoding reporter sequence may be used to monitor EPX promoter-mediated expression. The transgenic animals of the present invention that comprise the expression cassettes of the present invention also provide a means for screening analytes that may be capable of modulating expression mediated by the mouse eosinophil peroxidase (EPX) gene transcriptional control elements.

Methods of administration of the analyte include, but are not limited to, injection (subcutaneously, epidermally, intradermally), intramucosal (such as nasal, rectal and vaginal), intraperitoneal, intravenous, oral or intramuscular. Other modes of administration include oral and pulmonary administration, suppositories, and transdermal applications. Dosage treatment may be a single dose schedule or a multiple dose schedule. For example, the analyte of interest can be administered over a range of concentration to determine a dose/response curve. The analyte may be administered to a series of test animals or to a single test animal (given that response to the analyte can be cleared from the transgenic animal).

Thus, in one exemplary embodiment, transgenic mice carrying expression cassettes comprising eosinophil peroxidase transcription control elements, e.g., promoter, operably linked to a luciferase-encoding reporter sequence may be used to monitor the effects of a candidate compound on eosinophil peroxidase transcription control element meditated-expression. Transgenic mice of the present invention may be used to screen compounds which may be effective pharmaceutical agents.

The creation and phenotypic characterization of transgenic animals comprising eosinophil peroxidase gene derived transcription control elements (i.e., a transgene) is described in Examples 2 and 3.

Criteria for selecting a transgenic animal, e.g., rodent, useful in a model for screening compounds affecting the expression of, for example, the eosinophil peroxidase gene are generally as follows:

Criterion 1. Southern blot analysis and PCR analysis to identify transgenic animals carrying the transgene (e.g., EPX transcription control elements operably linked to coding sequences of interest, e.g., sequences encoding a reporter gene, for example, a light generating protein).

Criterion 2. Eosinophils from the transgenic animal express the coding sequence of interest, e.g., a reporter gene, at a greater level than other, non-eosinophil blood cell-types. Eosinophils as well as other blood cell-types are isolated from transgenic animals. The cell-types are fractionated (e.g., by FACs or panning) and reporter gene expression in the different cell-types is evaluated.

Criterion 3 (may be optionally applied). Induction of expression of the coding sequence of interest, e.g., a reporter gene, is observed by ovalbumin challenge via intraperitoneal injection or via airway inhalation. Induction is relative to basal levels of reporter gene expression in the unchallenged transgenic animal.

Criterion 4 (may optionally be applied). Administration of IL-5 to the transgenic rodent promotes trafficking of eosinophils, expressing the coding sequence of interest, to the esophagus of said transgenic rodent relative to other regions of the body of the living, transgenic rodent. When the reporter gene encodes a light-generating protein, such trafficking can be monitored by methods described in, e.g., Example 3.

Criterion 5 (may be optionally applied). Allergen-induced eosinophil cell recruitment to an air-pouch, e.g., a dorsal air pouch, of the transgenic rodent is reduced by glucocorticoid treatment (e.g., levels of expression of the reporter gene after allergen-induction are higher before treatment with dexamethasone than after treatment with dexamethasone). When the coding sequence of interest is a reporter gene that encodes a light-generating protein, such trafficking can be monitored by methods described in, e.g., Example 3.

Criterion 6 (may be optionally applied). At baseline (i.e., a transgenic animal maintained under healthy conditions), localization of expression of the coding sequence of interest, e.g., a reporter gene, is to the lamina propria (e.g., of the stomach and intestines), that is, greater expression of reporter gene is seen in the lamina propria relative to other regions of the body of the transgenic animal. Alternately, or in addition, greater expression of reporter gene in the lamina propria relative to other regions of the body of the transgenic animal (e.g., in the absence of interleukin (IL)-5 over-expression and/or oral allergen challenge).

Criterion 7 (may be optionally applied). Induction of expression of the coding sequence of interest, e.g., a reporter gene, is seen when IL-5 is over-expressed in the transgenic animal. IL-5 over-expression can be accomplished in the transgenic animal, for example, via direct protein injection, liver transfection (e.g., liver push experiments) or over-expression of IL-5 in the transgenic animal, where expression of IL-5 may, for example, be mediated by a constitutive, inducible, or repressible promoter.

The above-described optional phenotypic criteria may be applied, in addition to criteria 1 and 2, to transgenic animal screening singly or in combinations. Typically, at least one of the optional phenotypic criteria (e.g., criterion 3 and/or criterion 7) is applied for selection of a suitable transgenic animal (which carries and expresses a EPX-reporter transgene).

In one exemplary embodiment, transgenic mice carrying expression cassettes comprising the mouse eosinophil peroxidase (EPX) gene promoter operably linked to a luciferase-encoding reporter sequence, and meeting at least criteria may be used to monitor the effects of a candidate compound on EPX gene expression. The results of those experiments demonstrate that the transgenic mice of the present invention may be used to screen compounds which may be effective pharmaceutical agents.

2.5 Eosinophil Migration

Eosinophils are motile phagocytic cells that can migrate from blood into tissue spaces. It is believed that eosinophils play a role in defense against parasitic organisms. For example, the secreted contents of eosinophilic granules may damage membranes of parasites. However, although the release of these eosinophil-derived mediators may play a protective role in parasitic infections, in response to allergens, these mediators contribute to extensive tissue damage in late-phase reactions. The influx of eosinophils in the late-phase response has been shown to contribute to the chronic inflammation of the bronchial mucosa that characterizes persistent asthma. Eosinophils are known to be involved in several disease processes including, but not limited to, asthma, food allergies, and atopic dermatitis.

Asthma is a multifactorial syndrome characterized by breathlessness, pulmonary constriction, mucous accumulation, and airway hyper-reactivity. It is often, but not always associated with allergies (extrinsic) or environmental stimuli, e.g., tobacco smoke, but may also be induced by, for example, exercise or cold (intrinsic). Many pathophysiological manifestations of asthma are associated with airway infiltration by eosinophils and lymphocytes. Such infiltration is mediated by cytokines and chemokines. The extent of infiltration generally correlates with the severity of disease. Leukocyte influx has been associated with the development of lung dysfunction, even in nominal cases of asthma. Antigen-induced mouse models of pulmonary allergic disease have proved particularly informative in the genetic dissection of inflammatory pathways in the lung. Typically, these models involve sensitization with a specific antigen (e.g., ovalbumin) followed by airborne administration of the same antigen. Sensitized mice treated with aerosolized allergen develop leukocytic infiltrates of the airway lumen dominated by CD4+ lymphocytes and eosinophils. These mice also develop many of the changes indicative of asthma-related pathology, including airway hyper-responsiveness (AHR) and goblet cell hyperplasia typically with accompanying excessive mucus production. Accordingly, employing eosinophils marked as described herein, migration of eosinophils and other eosinophil responses may be studied in vivo in experimental animals. Further, the transgenic animals of the present invention, particularly transgenic rodents carrying coding sequences for a light-generating protein under the control of EPX regulatory sequences, will facilitate the analysis of important components of pro-inflammatory cascades that ultimately result in eosinophil airway infiltration and pathophysiological changes characteristic of asthma. In addition, the effects of selected analytes on eosinophil migration and response can be evaluated.

Cellular signals leading to airway inflammation, eosinophil infiltration, and airway hyper-responsiveness have not yet been completely elucidated. Lymphocytes, eosinophils, and mast cells have been implicated in airway hyper-responsiveness of antigen-challenged, mouse models of asthma. For example, SCID mice, lacking both T and B lymphocytes, develop neither airway eosinophilia nor bronchial hyper-reactivity (Corry, et al., J. Exp. Med. 183:109

(1996)). Further, depletion of CD4+ lymphocytes (e.g., by treatment with anti-CD4 antibodies or MHC Class II gene knock-outs) eliminated eosinophil airway infiltration and airway hyper-responsiveness in antigen-challenged mice (Garett, et al., Am. J. Respir. Cell & Mol. Biol. 10: 587 (1994)). However, depletion of CD8+ T lymphocytes with anti-CD8 antibodies had no effect on lung eosinophil infiltration but eliminated airway hyper-responsiveness (Nakajima, et al., Am. J. Respir. Cell & Mol. Biol. 10: 587 (1994); Hammelmann, et al., J. Exp. Med. 183:1719 (1996)). It also appears that mast cells were not specifically required for either eosinophil airway infiltration or airway hyper-responsiveness in a mouse model (Bruselle, et al., Am. J. Respir. Cell & Mol. Biol. 12:254 (1995)).

Transgenic animals which express a reporter, e.g., light-generating protein, under the transcriptional control of EPX regulatory elements can provide models for eosinophil-related disease states, as well as models for the efficacy of therapeutic agents which can be useful to treat those diseases. For example, transgenic mice expressing light-generating protein coding sequences under the transcriptional control of EPX regulatory elements can be useful as a model for diseases characterized by the presence of pulmonary eosinophilic infiltrations, including, but not limited to, the following: asthma (extrinsic or intrinsic), pulmonary eosinophilia, Loffler's syndrome, eosinophilic pneumonia, eosinophilic myalgia, atopic disease, e.g., allergies or asthma, emphysema, pulmonary fibrosis, Wegener's granulomatosis, lymphoidmatoid granulomatosis, eosinophilic leukemia, eosinophilic granuloma of the lung, adult respiratory distress syndrome, and post-trauma pleural effusions which contain eosinophils or eosinophil containing pleural effusions associated with infections, such as tuberculosis (see Spry, In: Eosinophils, Oxford University Press, pp. 205–212 (1988)).

The transgenic animals of the present invention, e.g., transgenic mice expressing light-generating protein coding sequences under the transcriptional control of EPX regulatory elements, can be useful as a model for atopic dermatitis, eosinophilic fasciitis, eosinophilia myalgia, contact hypersensitivity diseases, or other skin allergic or hypersensitivity reaction.

Furthermore, such transgenic animals can be employed as vehicles to test agents which are known to, or which may be useful to, reduce, inhibit, or other wise affect eosinophil migration. Agents which inhibit eosinophil-associated pathologies are known to the art and their in vivo effects can be evaluated using the transgenic animals of the present invention. In addition, new agents can be identified that affect eosinophil-associated pathologies employing the recombinant cells and transgenic animals described herein.

2.6 Screening Analytes

The methods of monitoring promoter activity discussed above may be employed for the purpose of screening analytes (e.g., candidate drugs) which modulate a variety of biological processes associated with expression of the mouse eosinophil peroxidase (EPX) gene. Screening may be accomplished by means of in vitro assays employing transiently or stably transfected cells, and may also be conducted using the transgenic animals of the present invention discussed above, either by themselves or in conjunction with other wild-type or transformed cells or tissues that have been introduced into those animals.

In one aspect of the invention, analytes which affect eosinophil migration or otherwise affect eosinophil-response in eosinophil-related pathologies (see above) can be screened for their affects using the recombinant cells and/or transgenic animals of the present invention. For example, the effects of an analyte can be evaluated in transgenic mice expressing light-generating protein coding sequences under the transcriptional control of EPX regulatory elements and eosinophil migration to the site of inflammation can be monitored in vivo, in real time, with and without treating the animal with the analyte. Such evaluation of analytes allows the identification of analytes useful, e.g., for the treatment of asthma.

The particular assay method used to measure the effects of various candidate compounds on eosinophil migration or EPX promoter activity will be determined by the particular reporter sequence present in the expression cassette carried by the cells or animals employed. As discussed above, promoter activity in transgenic animals carrying constructs employing reporter sequences encoding light-generating proteins may be measured by means of ex vivo assay methods or by means of the in vivo bioluminescent imaging technique reference previously. An animal eosinophil migration model will greatly enhance the process of validating analytes that are useful in the management of eosinophil-related disease states, that is, disease states where eosinophils serve as a marker.

In a further aspect of this invention, the expression cassettes and vectors comprising mouse eosinophil peroxidase (EPX) transcription control element sequences can be used to facilitate eosinophil peroxidase (EPX) gene expression regulation studies in vitro and in vivo. For example, regulatory sequences involved in the cell-type specific expression of the EPX gene can be identified. Specific locations of selected transcriptional control elements within a defined polynucleotide sequence can be identified by methods known to those of skill in the art, e.g., sequence comparison, deletion analysis, and/or linker-insertion mutagenesis, in view of the teachings of the present specification. Identification of regulatory sequences associated with cell-type specific expression allows, for example, the use of such regulatory sequences to confer cell-type specific expression to other promoters, e.g., a basal promoter.

For screening purposes, eosinophil cells may be transformed with an expression vectors comprising a reporter gene (e.g., luciferase) operably linked to the EPX gene promoters of this invention. The transformed cells are next exposed to various test substances and then analyzed for expression of the reporter gene. The expression exhibited by these cells can be compared to expression from cells that were not exposed to the test substance. A compound that modulates the promoter activity of the EPX promoter will result in modulated reporter gene expression relative to the control.

Thus, one aspect of the invention is to screen for test compounds that regulate (i.e., stimulate or inhibit) gene expression levels mediated by the EPX-locus derived transcription control elements (e.g., promoters). Screening may be accomplished by, for example, (i) contacting host cells in which the EPX promoter disclosed herein is operably linked to a reporter gene with a test medium containing the test compound under conditions which allow for expression of the reporter gene; (ii) measuring the expression of the reporter gene in the presence of the test medium; (iii) contacting the host cells with a control medium which does not contain the test compound but is otherwise essentially identical to the test medium in (i), under conditions essentially identical to those used in (i); (iv) measuring the expression of reporter gene in the presence of the control medium; and (v) relating the difference in expression between (ii) and (iv) to the ability of the test compound to affect the activity of the promoter.

In a further aspect, the present invention provides methods of measuring the ability of a test compound to modulate EPX transcription by: (i) contacting a host cell in which the EPX promoter, disclosed herein, is operably linked to a reporter gene with an inducer of the promoter activity under conditions which allow for expression of the reporter gene; (ii) measuring the expression of the reporter gene in the absence of the test compound; (iii) exposing the host cells to the test compound either prior to, simultaneously with, or after contacting, the host cells with the inducer; (iv) measuring the expression of the reporter gene in the presence of the test compound; and (iv) relating the difference in expression between (ii) and (iv) to the ability of the test compound to modulate EPX-mediated transcription.

Various forms of the different embodiments of the invention, described herein, may be combined.

Experimental

Below are examples of specific embodiments for carrying out the present invention. The examples are offered for illustrative purposes only, and are not intended to limit the scope of the present invention in any way.

Materials and Methods

Unless indicated otherwise, the experiments described herein were performed using standard methods.

A. PCR Amplification

For PCR amplifications, the reaction mix contained: 5 µl of 10× reaction buffer (no $MgCl_2$); 4 µl 25 mM $MgCl_2$; 0.4 µl of 25 mM dNTP mix; 0.5 µl of 10 pmoles/ul forward primer; 0.5 µl of 10 pmoles/µl reverse primer; 1 µl (0.2 µg) of DNA (BAC or genomic); 38.35 µl of $H_2O$; and 0.25 µl of Taq Polymerase (Life Technologies). The PCR was carried out as follows: 3 minutes at 94° C.; 35 cycles of 94° C., 45 seconds, 60° C., 45 seconds, 72° C., 45 seconds; 7 minutes at 72° C.; and stored at 4° C.

B. Southern Blotting (i) Primers were designed and used to PCR screen a mouse 129/SvJ genomic DNA BAC (bacterial artificial chromosome) library (Genome Systems, Inc., St. Louis, Mo.) in order to isolate novel mouse eosinophil peroxidase (EPX) gene promoter sequences.

A library containing, on average, contained inserts of 120 kb with sizes ranging between 50 kb to 240 kb was screened. A large genomic DNA fragment that contained EPX promoter region was obtained.

The EPX BAC DNA was isolated by CsCl ultracentrifugation and digested with various restriction enzymes for 2 hours. Digested DNA fragments were separated on a 1% agarose gel. The gel was depurinated in 250 mM HCL for 10 minutes and then denatured twice in 20×SSC with 0.5M NaOH for 20 minutes. DNA was then transferred onto Hybond N+ membrane (Amersham, Piscataway N.J.) with 20×SSC for 1–2 hours using a vacuum blotting apparatus (Stratagene, La Jolla, Calif.). After transferring, the membrane was cross-linked according to the manufacturer's directions using UV Cross-Linker (Stratagene, La Jolla, Calif.) and rinsed with 5×SSC. The membrane was then prehybridized at 60° C. for 1–6 hours with prehybridization solution (Stratagene, La Jolla, Calif.).

Probes were prepared by labeling PCR fragments or isolated DNA. After hybridization, the membrane was washed twice with pre-warmed 1×SSC, 0.1% SDS for 20 minutes at 60° C. each time. Subsequently, the membrane was washed twice with pre-warmed 0.5×SSC for 20 minutes at 60° C. each time. The membrane was blocked at RT for 1 hour using blocking solution (Stratagene, La Jolla, Calif.) and incubated with antibody conjugated to alkaline phosphatase for 1 hour. After three washed, substrate CDP-Star was added for 5 minutes. The membrane was exposed to X-ray film for between 1 minute and 3 hours.

C. Preparation of Transgenic Animals

The transgenic animals described below were prepared using the microinjection into single cell stage embryos (see, e.g., U.S. Pat. No. 4,873,191 to Wagner, et al. (issued Oct. 10, 1989); Richa, J., (2001) Molecular biotechnology 17:261–8. The embryos were implanted into pseudo-pregnant females and the offspring screened by PCR using primers lucF1 (GCCATTCTATCCGCTGGAAGATGG; SEQ ID NO:3) and lucR4 (CGATTTTACCACATTTGTA-GAGGTTTTACTTGC; SEQ ID NO:4). Imaging of animals was done as described herein.

D. In Vivo Imaging

In vivo imaging was performed as described previously (Contag, et al. (see e.g., Contag, P. R., et al., (1998) Nature Med. 4:245–7; Contag, C. H., et al., (1997) Photochem Photobiol. 66:523–31; Contag, C. H., et al., (1995) Mol Microbiol. 18:593–603); Zhang et al., (2001) Transgenic Res. 2001 October; 10(5):423–34) using either an intensified CCD camera (ICCD; model C2400-32, Hamamatsu, Japan) fitted with a 50 mm f 1.2 Nikkor lens (Nikon, Japan) and an image processor (Argus 20, Hamamatsu), or with a cryogenically cooled camera (Roper Scientific, Trenton, N.J.) fitted with a 50 mm f 0.95 Navitar lens (Buhl Optical, Pittsburgh, Pa.) available as an integrated imaging system (IVIS™ (Xenogen Corporation, Alameda, Calif.) Imaging System) controlled using LivingImage® (Xenogen Corporation, Alameda, Calif.) software.

The substrate luciferin was injected into the intraperitoneal cavity at a dose of 150 mg/kg body weight (30 mg/ml Luciferin stock) approximately five minutes prior to imaging. Mice were anesthetized with either Nembutal (25–50 mg/kg body weight) or in a gas chamber with an isoflurane/oxygen mixture and isoflurane tubing was placed on the animals' noses, and placed on the imaging stage under anesthesia. Mice were imaged from the ventral side for 1 minute. Relative photon emission over the liver region was quantified using LivingImage® software (Xenogen, Alameda, Calif.).

EXAMPLE 1

Isolation of Mouse Eosinophil Peroxidase Transcriptional Control Element Sequences and Vector Construction A pair of PCR primers specific for the mouse EPX promoter was designed (Primer 1, 5'-tgcatccatgaacccaagac-taga-3', SEQ ID NO:3; Primer 2,5'-cccactacagctaagcag-gcaagca-3', SEQ ID NO:4). PCR conditions were tested for specificity using the PCR conditions described above.

The PCR reaction using these primers was used to screen the BAC library described above. Two BAC clones were identified. One of the clones (MEPOXBA11k) was confirmed to comprise the EPX transcription control elements by sequencing. The plasmid MEPOXBA11k was sequenced from both ends and the sequence from one end matched the known sequence of the mouse EPX cDNA (GENBANK Accession No. D78353).

An XbaI fragment (10,985 bp) from the BAC was cloned into pBluescript-SK. Physical mapping was done on this plasmid. A restriction map of this clone is presented in FIG. 2. The sequence of 9,828 nucleotides of this clone, located upstream of the initiating ATG of the EPX gene, was determined. The sequence is presented in FIG. 1A (SEQ ID NO:1). A novel approximately 9.5 kb region of the EPX gene locus was identified from nucleotide position 1 to 9,450 of FIG. 1A and that approximately 9.5 kb sequence is presented alone in FIG. 1B (SEQ ID NO:2).

A vector for use in the generation of transgenic, non-human animals, was constructed as follows. An approximately 9.8 kb restriction fragment from the XbaI 10,985 bp clone was isolated by digestion with XhoI and partial digestion with BsrGI. The resulting approximately 9.8 kb fragment was cloned into the pGL3-Intron-Basic vector upstream of the human globin intron II which was upstream of firefly luciferase coding sequences (see below). The resulting vector was designated MEPO-luc. The sequence of the approximately 9.8 kb fragment corresponds to nucleotide positions 1–9,757 of FIG. 1A and are designated as SEQ ID NO:7.

The pGL3-Intron-Basic vector was constructed essentially as follows. An 861 bp fragment (including 849 bp human globin intron II and 12 bp exon-intron boundary sequence) was amplified by PCR from human genomic DNA. The accuracy of the intron, amplified product was confirmed by sequencing. The primers used were as follows: PCR Primer 1: 5'-agtcaagcttcagggtgagtctatgggacccttg-3' (SEQ ID NO:5); PCR Primer 2: 5'-gactaagcttaggagctgtgggaggaagataagag-3' (SEQ ID NO:6). A yellow-green luciferase with an emission peak of about 540 nm is commercially available in a plasmid vector from Promega, Madison, Wis. under the name pGL3basic. The PCR human globin intron II fragment was cloned into HindIII site of pGL3basic and the resulting vector was designated pGL3-Intron-Basic.

Table 1 indicates the sequences from the EPX gene locus, upstream of the protein coding region, which comprise the above described constructs. The starting and ending positions in Table 1 are given relative to the sequence presented in FIG. 1A.

TABLE 1

| Vector Name | Approximate Size of Fragment from the EPX gene locus | Starting Position of EPX gene locus fragment relative to FIG. 1A | Ending Position of EPX gene locus fragment relative to FIG. 1A |
|---|---|---|---|
| MEPO-luc | 9757 bp | 1 | 9757 |

This vector construct was used to generate transgenic mice as described in Example 2.

EXAMPLE 2

Transgenic Animals

Transgenic mice were generated essentially as follows. The MEPO-luc plasmid was digested with NotI and XhoI. The resulting fragment containing mouse EPX promoter and luciferase was separated by size-fractionation using an agarose gel. The fragment was then isolated from the agarose gel. The purified DNA was injected into fertilized eggs of FVB mice (Charles River Laboratories, Inc., Wilmington, Mass.). The transgenic lines were created by the microinjection method (see, e.g., U.S. Pat. No. 4,873,191 to Wagner, et al. (issued Oct. 10, 1989); and Richa, J., (2001) "Production of transgenic mice" Molecular biotechnology March 2001 vol. 17:261–8) using FVB donor embryos. The injected eggs were transplanted into pseudo-pregnant female foster mice following standard procedures (e.g., Methods in Enzymology, volume 225, page 747–771, edited by Paul M. Wassarman & Melvin L. DePamphilis.). The resulting mice were screened for the presence of the EPX/luciferase sequences by PCR as described above. Alternately, the founder mice are screened by PCR using luciferase primers LucF1 and LucR4 or primers Luc 3 primer (5'-GAAAT-GTCCGTTCGGTTGGCAGAAGC-3' (SEQ ID NO:8)) and Luc 4 primer (5'-CCAAAACCGTGATGGAATGGAA-CAACA-3' (SEQ ID NO:9)). These same primers may also be used to screen Tg offspring.

Transgenic founders and transgenic offspring may also be evaluated for the presence and location of the transgene (e.g., an EPX transcription control element operably linked to a reporter gene, for example, a light-generating protein) using Southern Hybridization Analysis.

For example, the 1.8 kb HindIII/XbaI fragment from pGL3-Basic containing the entire luciferase cDNA (Promega Corp.) is used as probe for Southern hybridization. Ten μg of heterozygous genomic DNA is digested with a selected restriction enzyme (e.g., BamHI) and 17 pg of pGL3-Basic was loaded as a positive control. The expected size of transgene is calculated based on the known restriction map of the construct used to generate the transgenic animals. Results from such Southern analysis can be used to demonstrate the presence of the transgene in the transgenic mice.

These mice are then used as founders for a transgenic colony.

EXAMPLE 3

Phenotypic Data as Applied to Selection Criteria

General Methods

In vivo imaging was performed as described previously (Contag, et al. (see e.g., Contag, P. R., et al., (1998) Nature Med. 4: 245–7; Contag, C. H., et al., (1997) Photochem Photobiol. 66:523–31; Contag, C. H., et al., (1995) Mol Microbiol. 18:593–603); Zhang et al., (2001) Transgenic Res. 2001 October; 10(5): 423–34) using either an intensified CCD camera (ICCD; model C2400-32, Hamamatsu, Japan) fitted with a 50 mm f 1.2 Nikkor lens (Nikon, Japan) and an image processor (Argus 20, Hamamatsu), or with a cryogenically cooled camera (Roper Scientific, Trenton, N.J.) fitted with a 50 mm f 0.95 Navitar lens (Buhl Optical, Pittsburgh, Pa.) available as an integrated imaging system (IVIS™ Imaging System, Xenogen, Corporation, Alameda, Calif.) controlled using LivingImage® software (Xenogen, Corporation, Alameda, Calif.).

The substrate luciferin was injected into the intraperitoneal cavity at a dose of 150 mg/kg body weight (30 mg/ml Luciferin stock) approximately five minutes prior to imaging. Mice were anesthetized with either Nembutal (25–50 mg/kg body weight) or in a gas chamber with an isoflurane/oxygen mixture and isoflurane tubing was placed on the animals' noses, and placed on the imaging stage under anesthesia. Mice were typically imaged from the ventral side for 1 minute. Relative photon emission was quantified using LivingImage® software (Xenogen, Alameda, Calif.).

These imaging methods can be used to track events in a test subject over time. For example, a compound may be administered to a subject (comprising a light-generating reporter), and photon emission from the subject before, during, and/or after administration of the compound may be measured. Such measuring may be repeated at selected time intervals which is typically effective to track an effect of the compound on a level of reporter expression in the subject over time.

General methods for evaluating the transgenic animal lines were as follows. Tg founders were bred to wild-type FvB mice to generate F1 mice. A female transgenic founder is typically bred to a wild-type FvB male and a male transgenic founder is typically bred to a few wild-type FvB females.

A Luciferin stock solution of 30 mg/ml was prepared in sterile PBS. Luciferin was purchased as D-Luciferin Potassium Salt, as Cat # XR-1001, from Biosynth AG, Switzerland.

Dexamethasone (Cat # D1756), may be purchased from Sigma (St. Louis, Mo.) and may be prepared in a solution of DMSO and injected IP at a dose of between about 1–150 mg/kg. DMSO is administrated as a vehicle control. The duration of treatment with dexamethasone is typically for hours, 2–3 days, up to about 7–10 days. Alternately, dexamethasone may be subcutaneously administered (see, e.g., Das, A. M., et al., Br J. Pharmacol. 1997 May, 121 (1): 97–104, herein incorporated by reference).

The route of administration for luciferin is, typically, IP. The dose of reagent administration of luciferin substrate was as follows. Dose of luciferin: 150 mg/kg of a 30 mg/ml luciferin stock was injected IP five minutes before imaging in the IVIS™ (Xenogen Corporation, Alameda, Calif.) system.

Following luciferin administration the animals were anesthetized using gas anesthesia (Isoflurane) and placed in an IVIS™ box (Xenogen Corporation, Alameda, Calif.) for imaging. All animals were imaged before and after chemical administration, and imaged at high resolution (binning 2).

Phenotyping

As discussed above, the following phenotypic criteria are applied to the selection of transgenic animals for use in methods of the present invention:

Criterion 1. Southern blot analysis and PCR analysis to identify transgenic animals carrying the transgene (e.g., EPX transcription control elements operably linked to sequences encoding luciferase).

Southern blot analysis and PCR analysis are performed essentially as described above.

Criterion 2. Eosinophils from the transgenic animal express luciferase at a greater level than other, non-eosinophil blood cell-types. Eosinophils as well as other blood cell-types are isolated from transgenic animals. The cell-types are fractionated (e.g., by FACs or panning) and reporter gene expression in the different cell-types is evaluated.

Methods of cell fractionation (e.g., FACs and/or panning) are known in the art (e.g., Shinagawa, K., and Anderson, G. P., J. Immunol. Methods 2000 Apr. 3 237(1–2):65–72; Fattah, D., et al., Cytokine 1996 March 8(3):248–259; Hoang, T., et al., Blood 1983 March 61(3):580–588; Hunt, T. C., et al., Clin. Exp. Allergy 1993 May 23(5):425–434; Burgess, A. W., et al., Exp. Hematol. 1980 January 8(1): 108–109; all herein incorporated by reference in their entireties) and may be applied to phenotyping in view of the teachings of the present specification.

Criterion 3 (may be optionally applied). Induction of luciferase signal is observed by ovalbumin challenge via intraperitoneal injection or via airway inhalation. Ovalbumin challenge models are known in the art and may be applied to phenotyping in view of the teachings of the present specification. See, for example, Liu C, Wang Z, Liang Z, Lei S, Chin Med J (Engl) 2000 September 113(9): 783–6; Tomkinson A, Duez C, Cieslewicz G, Pratt J C, Joetham A, Shanafelt M C, Gundel R, Gelfand E W, J Immunol 2001 May 1 166(9):5792–800; Tomkinson A, Cieslewicz G, Duez C, Larson K A, Lee J J, Gelfand E W, Am J Respir Crit Care Med 2001 March 163(3 Pt 1):721–30; Cui X, Guo Z, Xu W, Chen Y, Zhu Y, Chin Med J (Engl) 1998 October 111(10):940–4; Trifilieff A, El-Hashim A, Bertrand C, Am J Physiol Lung Cell Mol Physiol 2000 December 279(6):L1120–8; Trifilieff A, El-Hasim A, Corteling R, Owen C E, Br J Pharmacol 2000 August 130(7): 1581–8; Blyth D I, Wharton T F, Pedrick M S, Savage T J, Sanjar S, Am J Respir Cell Mol Biol 2000 August 23(2): 241–6; Dohi M, Tsukamoto S, Nagahori T, Shinagawa K, Saitoh K, Tanaka Y, Kobayashi S, Tanaka R, To Y, Yamamoto K, Lab Invest 1999 December 79(12):1559–71; all herein incorporated by reference in their entireties. Induction is relative to basal levels (i.e., pre-ovalbumin challenge) of luciferase expression in the unchallenged transgenic animal.

Criterion 4 (may optionally be applied). Administration of IL-5 to the transgenic rodent promotes greater trafficking of eosinophils to the esophagus of said transgenic rodent than to other regions of the body of the living, transgenic rodent (see, e.g., Mishra, A., J. Immunol. 2002 March 1, 168(5): 2462–2469; Mishra, A., et al., J. Clin. Invest. 2001, 107: 83–90, both herein incorporated by reference). The trafficking is monitored by tracking expression of the coding sequence of interest (e.g., luciferase). Such tracking can be performed over time. Luciferase expression in intact, living, transgenic rodents can be monitored as described herein above.

Criterion 5 (may be optionally applied). Allergen-induced eosinophil cell recruitment to an air-pouch (e.g., dorsal air pouch) of the transgenic rodent is reduced by glucocorticoid treatment (see, for example, Das, A. M., et al., Br J. Pharmacol. 1997 May, 121(1):97–104, herein incorporated by reference). In one embodiment, levels of expression of luciferase after allergen-induction are higher before treatment with dexamethasone than after treatment with dexamethasone. Dexamethasone may be administered, for example, at an amount of between about 1–150 mg/kg body weight of the transgenic animal, preferably between about 2–10 mg/kg body weight. The dexamethasone can be administered following a predetermined treatment schedule. Dexamethasone can be administered IP or subcutaneously. Use of luciferase as a reporter gene permits such trafficking to be monitored by methods described herein above. The reduced recruitment to the air-pouch is observed, for example, by a reduction of the level of expression of the coding sequence of interest (e.g., luciferase) in the region of the body of the transgenic animal corresponding to the air-pouch.

Criterion 6 (may be optionally applied). At baseline (i.e., a transgenic animal maintained under healthy conditions), expression of luciferase is localized to the lamina propria (typically of the stomach and intestines), that is, greater basal expression of luciferase is seen in the lamina propria relative to basal expression in other regions of the body of the transgenic animal. Alternately, or in addition, greater expression of luciferase may be seen in the lamina propria relative to other regions of the body of the transgenic animal, for example, in the absence of interleukin (IL)-5 over-expression and/or oral allergen challenge. In addition, levels of eosinophils can be induced by antigen exposure under Th2 conditions (see, for example, Rothenberg, M. E., et al., Immunol. Rev. 2001 February 179:139–155, herein incorporated by reference).

Criterion 7 (may be optionally applied). Induction of luciferase expression in the transgenic rodent is seen when IL-5 is over-expressed in the transgenic animal (relative to luciferase expression when IL-5 is not over-expressed). Van Oosterhout, A J, et al. (Am Rev Respir Dis 1993 March, 147(3):548–52, herein incorporated by reference) describe that treatment with IL-5 for seven days tends to increase the number of eosinophils in bronchoalveolar lavage (BAL) fluid. IL-5 over-expression can be accomplished in the transgenic animal, for example, via direct protein injection, liver transfection (e.g., liver push experiments) or over-expression of IL-5 in the transgenic animal, where expression of IL-5 may, for example, be mediated by a constitutive, inducible, or repressible promoter.

Coding sequences of IL-5 are known for many animals (e.g., Campbell, H. D., et al., Eur. J. Biochem. 174 (2), 345–352 (1988); and GenBank Accession Nos. AJ011299, U34588, and X06271). Suitable expression plasmids/vectors are known in the art. For liver push experiments, plasmids may be administered by intravenous injection according to the method of Liu F., et al., (1999) Human Gene Therapy 10:1735–1737. For example, a 2.2 ml of a PBS solution containing the desired IL-5 containing-constructs are injected into the tail vein over a period of less than 8 seconds.

The above-described optional phenotypic criteria may be applied, in addition to criteria 1 and 2, to transgenic animal phenotypic screening singly or in combinations. Typically, at least one of the optional phenotypic criteria (e.g., criterion 3 and/or criterion 7) is applied for selection of a suitable transgenic animal (which carries and expresses a EPX-luciferase transgene).

Accordingly, transgenic rodents (e.g., mice), comprising EPX transcription control elements operably linked to luc coding sequences, having desirable phenotypes, as outlined in the above criteria, can be identified by the methods taught herein.

The eosinophils of the resulting transgenic rodents are labeled with luciferase (i.e., expression of luciferase is mediated by eosinophil-specific eosinophil peroxidase transcription control elements). This transgenic rodent model is used to monitor eosinophils in vivo, for example, employing methods of inducing disease conditions like Asthma, Chronic eosinophilic pneumonia, Allergic rhinitis and Atopic dermatitis. The inducing agents employed can be either biological molecules or chemical compounds. These transgenic rodents are then used as models to, for example, evaluate the effect of test compounds on such disease states.

As is apparent to one of skill in the art, various modification and variations of the above embodiments can be made without departing from the spirit and scope of this invention. These modifications and variations are within the scope of this invention.

What is claimed is:

1. A method for identifying an analyte that modulates expression of a sequence encoding a light-generating protein, wherein expression of said light-generating protein is mediated by transcription control elements derived from a mouse eosinophil peroxidase gene, in a living transgenic mouse, said method comprising providing a living transgenic mouse whose genome comprises an expression cassette comprising a polynucleotide having nucleotides 1 to 9,825 of SEQ ID NO:1 or a variant thereof that have at least 95% or greater identity to nucleotides 1–9,825 of SEQ ID NO:1 over the entire length of nucleotides 1–9,825, operably linked to a sequence encoding a light-generating protein, wherein the polynucleotide causes increased expression of the light-generating protein in eosinophils of the living transgenic mouse as compared to non-eosinophil blood cell-types;

administering to the living transgenic living mouse said analyte; and monitoring expression of said light-generating protein wherein an effect on the level of expression of said light-generating protein indicates that the analyte affects expression mediated by transcription control elements derived from the mouse eosinophil peroxidase gene.

2. A method for monitoring eosinophil cell location in a living transgenic mouse, said method comprising providing a living transgenic mouse whose genome comprises an expression cassette comprising a polynucleotide having nucleotides 1 to 9,825 of SEQ ID NO:1 or a variant thereof that have at least 95% or greater identity to nucleotides 1–9,825 of SEQ ID NO:1 over the entire length of nucleotides 1–9,825, operably linked to a sequence encoding a light-generating protein, wherein the polynucleotide causes increased expression of the light-generating protein in eosinophils of the living transgenic mouse as compared to non-eosinophil blood cell-types;

inducing eosinophil production in the living transgenic mouse, and monitoring eosinophil cell location in the living transgenic mouse by monitoring locations of expression of the light-generating protein in regions of the body of the living transgenic mouse.

3. The method of claim 2, wherein said monitoring is carried out over a series of time intervals.

4. The method of claim 3, wherein said monitoring is begun before inducing eosinophil production.

5. A method for evaluating the effect of an analyte on eosinophil migration in a living transgenic mouse, said method comprising providing a living transgenic mouse whose genome comprises an expression cassette comprising a polynucleotide having nucleotides 1 to 9,825 of SEQ ID NO:1 or a variant thereof that have at least 95% or greater identity to nucleotides 1–9,825 of SEQ ID NO:1 over the entire length of nucleotides 1–9,825, operably linked to a sequence encoding a light-generating protein, wherein the polynucleotide causes increased expression of the light-generating protein in eosinophils of the living transgenic mouse as compared to non-eosinophil blood cell-types;

inducing eosinophil migration to a selected site in first and second living transgenic mice, administering to the first living transgenic mouse an analyte, monitoring eosinophil migration to the selected site in the first and second living transgenic mice by monitoring expression of the light-generating protein in the living transgenic mice, and evaluating any effect of the analyte on eosinophil migration by comparing eosinophil migration in said first and second living transgenic mice.

6. A method for inducing eosinophil, cell-type specific expression of a coding sequence of interest in a living transgenic mouse, comprising inducing eosinophil production in a living transgenic mouse whose genome comprises an expression cassette comprising a polynucleotide having nucleotides 1 to 9,825 of SEQ ID NO:1 or a variant thereof that have at least 95% or greater identity to nucleotides 1–9,825 of SEQ ID NO:1 over the entire length of nucleotides 1–9,825, operably linked to a sequence encoding a light-generating protein, wherein the polynucleotide causes increased expression of the light-generating protein in eosinophils of the living transgenic mouse as compared to non-eosinophil blood cell-types;

wherein said induction of eosinophil production results in eosinophil, cell-type specific expression of the light-generating protein in the living transgenic mouse.

* * * * *

SEQUENCE LISTING

```
<160> NUMBER OF SEQ ID NOS: 11

<210> SEQ ID NO 1
<211> LENGTH: 9828
<212> TYPE: DNA
<213> ORGANISM: Artificial Sequence
<220> FEATURE:
<223> OTHER INFORMATION: Description of Artificial Sequence:
      transcriptional control element from the mouse EPX gene locus

<400> SEQUENCE: 1
ttctcagatg gtatgatttg acacagagct gggattatct ctgaaaggtt gtggggtgac      60
tttatgtatt aggctaaaca ccactccatg actctcagca gatgccaaat acctttaaat     120
tttgattttg tcactcagtg tggtggtcag atatgtttga aggcttcgtg gaaattagca     180
aaggttccgc ctctatggga ctgatgtaac tcagagaaac cagagaatac cacccggaga     240
gcaaaatgca ggctggcttg caatccccac atcctctcct gattaaactg ttaactttac     300
actctgactc tgacattcat gattttatgt gttttgagtt gctaacatgc aaaaatgcac     360
aactgtgggc cttttcttc ttttctattt tattttatta tttttattat ttaattaatt     420
ttttacactc catatttat tcccccatc caccctccaa ctgttccaca tcccatacct     480 cctcccacc cccctgtctc catgtggatg tccccacccc cgtcccacct gacctctaaa     540
ctccctgggg cctccagtct cttaagggtt aggtgcatca tctctgaatg aacacagacc     600
tgaaagtcct ctactgtatg tgtgttgggg gcctcatatc agctagtgta ccctgcctgt     660
ttgatggtct aatgtttgcg agatctcggg gtccagatta attgagactg ctggtgctcc     720
tataggatca cccttctcct cagcttcttt cagccttccc taattcaacc acagggtca     780 gctgcttctg tccactggtt gggtgcaaat atctgcatct gattctttca gctgcttgtt     840
gggtcttcca gagtgtggtc atgacaggtc ccttttttgta agctctccat agcctcagtg     900
atagagtcag gccttggaac cttcccttga gctggatctc actttgggcc tgtcgctgga     960
```

```
ccttcttttc ctcaatatcc tctccatttc catccctgta attctttcag acaggaacaa      1020
ttatgggtca gagatgtgac tgtgggatgg caaccccatc cctcacttga tatcctgtct      1080
tcctgctgga ggtgggctct gtaatttccc tcttctactg tcctgcagtt catctaaggt      1140
cccttccttt gagtcccgag agtctctcac ctcccaggtt tctggtgctt tatggagggt      1200
ccccccaacc ttctatctcc tgaggttgcc tgtttccatt cttctgctg ccccttaggg       1260 cttcagtcct tttccctcac ccaataccag atcaggttcc ccttcttccc ccctcccccc      1320 ccccggggg ggggcttttc ttatagagga actgtgttgg ttgtatgtgt gcactggaat       1380
gtatgagtat gcatgtgtgt gtgtgtgtgt gtgcatatgt atggaggcca gatgtcaacc      1440
ctggacattt ttttcttaga catggtcaat cttgctttaa atcttttttt tttttaatta      1500
tttttaaatt gcgaatctat ttgtgcatgt gtgtgcagta cctattaagg ccagtagagg      1560
gctcaagagc tcccggagtt ggagttacag gcggttgtga attgccttag gagcttagga     1620
tgcttagaag ctctctctct ttgttttga gacaagacaa gcgctttcat taggacttgg      1680
gacttgttga ttaggttcag tggccattgt acctcagggg tactccagcc tctccctccc     1740
caacacaggt gtgctgcctc gcctggctta aaaaaaaaat taaaattaaa aaaaaaatgt      1800
gggccgggca atagtggcac acacttttaa tctcagcact gggagacag aggcaggcag       1860 atctccaagt tccaggacag ccagagcagc taggcatggt gggacacatt ttcaatccca      1920
ccactgatga agcagaggta gatttctgta agttctatgt ggtaagttct gggacagcca     1980 gggattttt ttttttttt agtgagtgcc tgcacacatg catgtgcatc gtgtgtgtct        2040
ggtacccaca gagggcatca gattgcctgg agttagcatt acaggtgttt ctgtgcttcc      2100
taactctgac tttggctttg tgtgtgagca gcaagtgctc ttagcttagg agccctctat      2160
ccagacctcc atgtctggtt tctcaggtgg tttccaggga tagaacttgg gtcctcctgt      2220
tcaagcagca agctctccct caccctatgc tggtccttta ttgaatacaa gtgagcccag      2280
gggacctgag gaggacgcag gcttccctgt cagattccca tcaaccccta ctctgggggc     2340
cttctttctc cacaagctca acagtcagcc tagcaatcct catccaggag gctgtatagg      2400
gaattcgtct ctccagacca gctgcagagt taggactgac ccttcctgcc ttttgctgac     2460
ttgattagca gttcagagag atcaagttct tgctcaaagc cacacaggtg ggtcaagcca     2520
tgacagaagt gggagtagtg ctggacttcc agccagctct ccagagcccc aagctgcact      2580
gtcagacttg gtgagtaaag gcaaggaact cagagctgtc ttttcagaac aacacacaca      2640
cacacacaca cacacacaca cacacacaca cacacacaca gagagagaga gagagagaga      2700
gagagagaga tgcagacaga tacacatata cagacacaca gacacataca tagacacata     2760
cacagttgca gacagacaca caaacagaca tatacagaca cacatataca gacacataca     2820
tagtcaaaca cacacccaga tgcagacaca cagacacata caaacacaca cacacacaga     2880
cacagaaact cagagacaca tacaaacaca cacacagata cacacagaaa cacagtcaca     2940
gacatacagg cacacagaga gacacacaca gaaacacaca gtgacacact cacacacaga     3000
cacaccatca tacacacaca gtggtgcaca cagacacatg cacacacagt gacacacaca     3060
gagagacaca cacacatcag cctctggcac agtgtgctgc cactaaggtt taggcaagct      3120
ccctttccat gcatctctca gtgttctcaa agttacacca ggacaaatga ccccctttcc     3180
aaagaaaccc tgggagcaag ggtgggtctg ccaagcctga gccttgctgt gtcccctgtc     3240 ttaatgggc agttggagca gagcagataa agagatccga tcaggcctgt ggccagcagt      3300
tccaccatgg cgggtagaca gttcttgtga aagtgattgc agaaggatga ggtttcagac     3360
```

-continued

```
tgcccaggga ggaggggagg ggaggtcctc cagtgctgcc gattaagagt cctgagaaag   3420
aagctgtcct catggtccat ggcctggtct gccacagcat ccagtgaccc acagcaaggc   3480
tggtccaggg atggccctta ccataggtac tgggtcctga catgcacggg cacaaatcca   3540
tctcctgacc aacagcaat ggcaggcaag gtcacagcaa acacatctgc tccacaaatc    3600
ctaccaggcc tgccaggcac acctaggtag gaggctactg tgggcaaacg ccttttctgt   3660
gcggaacttg aggagcgtat tggattcata agcacatgat gaattttgga agaaactgt    3720 gagactaaga accagagggc ctaagcctgc cgagtcttgg aaggattccc tgtggatgag   3780
tgagacctag gaactcagtg ggagtcagcc aggcggagac aaagagcctt cagggcttgc   3840
gacttgtgtc tgtctgaaag atggtagact ttgctatgaa gctgaaagcc agtgtgctta   3900
ggaagcagag gaataggttt accctgcagg tgaggcagga gccagggttc tgagatggag   3960
ggagggaagc aggcagccca agcaagcaac tgaggagctg aatggtcagg gctccacatc   4020
ccaagcactc ctagaagcct tgtcacccca aaataataat ctcttcctca cccccttcct   4080
cctctttctc ctcagtgctg ggcatggaac gcagccttga aatcgtccc agccctaagt    4140 acggtccccc tcacaggtcc tgagtggccc tgcctcattg ttttttatttt ggccatttcc  4200 ctataggagg aagggcttgc ctgtgagatc cccaagccta tggccttgtc attgctggaa   4260
ggaaatgtat ctaccccaga agcaggttct gggttccact tgctgaggga agagctctca   4320
tatcagcctc atagacaggc agcttcccta acacccaacc aggaggatat accctggct    4380 cctacttagt ggtctgcgca ccctctcttt tctctgctgg ttcaggctct gccctccacc   4440
ctggatctgt agcctaactg gccctggag aaggaagaga actggagaaa tcccaactag    4500
gtcagggagg ggatttgttt tttcttgcta gggtggactt agtgggttaa gcaagaaagc   4560
tactcgctct cttctgagac ctggcccag gcctctgctg agtgttgact acacaccata    4620
gagatcaagt acggagcctc ttctcccacg cattcagaag accaatggac gtggtgacgt   4680
cattccttcg ttaaagttca atatgtgctg agaaacatca gtgctgagaa acatcactgt   4740
ggggtgcccc atagatcaaa gagggacatc agagatgtct ttggaggcga gcagaaagtg   4800
gccaacggaa ggccttctgg ctgaggttag ggtaaaatga gtggagttat ctggcaaca    4860 aggactgcga atgatctag aagtggggga agggcacatc cattaaggct ggggtgtggt    4920
ggatggtggg gaggaacgat agtggaggct agggagaagc tgtgagcctg aggggggtgtg  4980 gaagcattgg ggctcctgct gctcaataga ccaggtcact gtgcacccag cccttcccct   5040
ccctgggtgc tcagaaccca gtgattccct cctcactcaa aatacatgga ccggtgggtt   5100
gtggagggag tagaaagcct cctgttttgt cgctaatgaa ggagcaaagc gagctgttca   5160
cccttgcaca aaagctaagg ggttccgtga acccttgga gtcattaccc cagggaatca    5220
ttaaacaagg tcaggtggct cttgaggtcc actctgccgt tgttactcta aacaatcgca   5280
gcaataaaat tctcctcccc aagtacagtt tgtgccgctc tatatgctaa gtgattgctg   5340
ccaatactgt ttaactttaa taaccccgt gagttcaagt cagtgggttt ttttttttta    5400
ttgcgcataa gaaccgtggt taatttagga agttcccagt tatacaatgg ctgcctctgc   5460
tgtgtgcgtt tacttcaaga gtaaggacaa agctgtgcac gattgtattt acacatttca   5520
cttgcctggg gatgtatctc tgctgaaaga gtgcttcctt agcatacaca aggtcctggc   5580
aatccctggc accacatgaa ctgggggtgt gggtggggtg gaatatgcct gtaaccccag   5640
cactgggtag gagtgattag gagaagccaa agttcaaggt catcttggc tacatagcaa     5700
```

-continued

```
gtttgaagct agcctagact acgtgaaacc ctgtctcaaa caaaacaaaa aatagttgat      5760
ataaatgata gcacagtact tataaagttg aagaaaatag aatctgattt ccttttaatt      5820
ctgttgttct acgtgaaggc tggcattta  attaatataa gattcaagtt taaaacagtg      5880
tgtgaaaact gtatctttta aaagatata  tttttattaa gttttaactt cttgtagata      5940
tacacatatc tgtgtgtagg tgtgtgcata caggcgccct gggaatccag agaagggcat      6000
tggatcccct ggagctggag ttacaggcct ggaagctgtt gaatgtaggt gctgggaaca      6060
gaacccgggt cctctggaag tgctctaagc cactgagcca tctccccagc cctggaaaca      6120
gtatcttcct gtacaactga cttcacatgt gaaatggttt tacgggtttt ttatgccttc      6180
aagattgagc tgtttcttct ctttaaacgc ccgtttgtct gttttttggga tgcccctgct      6240
gcgtagctca gggcgatctc taactgcatc agtctcccac gtgttgggat ggcagcggtg      6300
tgccgccgca cctggtggaa ctgctgactc taaaactaaa aagaaatttt agtacttaac      6360
tatattttga atactaaagc tgctaatata agccaggtgt gtgtgttatc acacatctgt      6420
aattttggcc cttgggaggg ggaaggagga ggaagagttt caagccagcc aggacttcat      6480
gaggttctgt tccaaacacc taaaccaacc aaccaccacc accaccacca acaaaaatct      6540
aacaatatgt ggatatttcc ccttaagtta aaaacattaa gccattacat ttttccttt       6600
atatagttag tatgtttgca tgcatgcatg tatttgttta tttccagagt ctcatgcatt      6660
ttagactgat ctctaacttc ctgtgtagct gtggcagacc ttgaacttca atctttcagc      6720
taatatatat tatgtattat atatatatgt atgtatgtat atatatatat ataatacata      6780
atatacacac atacatacat acacaatata tatatacaca cacatttata tatacacaca      6840
tacatacaca atatatatac atatacatat atatatacac atacacacat atacatatat      6900
attttactga cacaattata tacattaaga tcaataaaag aaaacctcct cacatttctg      6960
gccattacta tttgtttcat ttaatgagta tcttcaaaa  ttattttaat gggtagagga      7020
ggatactgaa ggaggcccta gtgtctgaca cacttcgttg ctactggaca aaacttagct      7080
acaaggaaaa tctctcctat gagttgctga gagaaaagac tcatgggaaa gcctgagaac      7140
ccatagtctt tgcccacact cctcccctgg tccctctgat cacgacaact aagaagaaag      7200
tcaatgtcag agctgactac catgagcatg tgcggaccct gcctgtctgt cagacctgtc      7260
acagtgaagg ccacagtggg tgcctaggct ggagggcacc tcaccttgtc cagggctcca      7320
tcttcatcag gtccctgtgg cctcagcccc agaactaggt gccaatgcct tcattttaga      7380
ggcctcccct ttagaaatct agccctgaag gatccaaaga cgcttttgca ttcttcgctc      7440
ctgcctccca gctgaagcca atggctgcct gaggggacag ccccgtgtaa aggtaacaaa      7500
gaagcaacaa taagatagaa caatgaggct tcttcagtgc cctgcttgcc aggcactgtg      7560
gtggtgtgtc acatgttcta ccaggagcta gggaaacctc cactgtgcag gagaaggcct      7620
ttaggcccag cacttgcctc acaggatgat gggattgtat caggagctct tgaggacttc      7680
tttgagctgc tctcagggggg ctccttggtg ctgagtacag gatttaggtc ccagcttgat      7740
ttgagagggg tcagacgtg  gcatcctaga gggagctagg caaaggggat ggcattcatc      7800
aaagggagag gatcataaac agaagattag catggttggt gctctggaca gggtcccgta      7860
ggagagcagc tgagtgtaag gtgaagggag cacgtggccc caggggttag aagagccatg      7920
tgacaagcca tacttcttca gtctcctgaa tgagctttac ccactagtcc agacccaaga      7980
ggcagcttaa gcaacatccc cagaacttgc cttccacagt cagggtctgt agggtccctc      8040
aggctctcag tcaaatcttt aagcctaact tgttaagata cccaaatata acaaatgtag      8100
```

```
caggtaggga tggatctaga gcccagtgct ctgcccctgg ttcatccccc aaactcactg      8160
cattccatcg ctaggaccac tctcaactaa ctggctgctg ttaaagaact aatgacccct      8220
ttaggggaga gcagagttct gtgggggtat ggcgtccctg gaaggagggc atcctagctc      8280
tagcctgggg catctggagg ggagggaaag ctcagctgtg catggtaccg tttaaaatct      8340
cttgggatca ccattctggc tcttaagctt ggaaacggag gtctagcagg gtatgtcggg      8400
agatctagtc gaccttcatc cttccttgta attttgtatc ccttggcaaa caggttcggc      8460
ctctgctgaa gatgggagat aagataggggg aagccttgcc aacaggagct tgtgaaagga      8520
gttgctaaag caaaatggct gtttcaggag caactgttga ggccggtggc agaggaggga      8580
gcactgatga gggaggagga agcactgatg cgggaggagg ggcaggggaa ggcgttgtgc      8640
aggttgaggt gggacagggg ttgaagagcc cggggaagag tctcctgagg tctaggaagg      8700
aatggacatg ctcacctgaa gggaccagga taggttggtt accagcacag tggcagtggc      8760
tttggagcca gagaccaaca ctagccatca aggcaggcaa ggatcaacag ctcctccag       8820 agaagggcct gtcagaagga aaggcttgaa agtgtgaagg aaggagctgc ggcccgactg      8880
agttgagttc tgcccaagat ctcactgcct gtgaaagagc cagatggaga ctcaggtcag      8940
tcaggcctag tgcagcaatc tctttcacgg gagcacacag taagcccacc actgctgtgc      9000
attgagagga gatcagggca cgctcagagc cacagtgagc ctttaggtct gggcaggaag      9060
cttccagcag ttcactcgct gtgagttcta cctgtgacac ctcaccatga ccccaggtgt      9120
cccctgaggt atttctctgg catcttggag ggagcagatc gccctaggga gataaggaga      9180
gaactggatt attgacgact cactcctcta caaacattta atgaacgcct actgaatgga      9240
gccttgtgct gagtattagg ggtatggtaa tatgtctgga ccccctttct gccctgatgg      9300
ggagagagga acctttccaa acatccacac aaaacctatt ttagggatgt gaaaatgagt      9360
gacaattagc gatggggcca agctctctct ttttgtcagt aacgaggtca ttcatcactc      9420
attgggtgac acctccatcc ccagcactgc ttcgggttgt gggggcaaa tgcatccatg      9480 aacccaagac tagaggtggg tgtggaacaa ggtaatggtg gctaggggag cccccattct      9540
ggtgagttgg taaagtatga tgggggtgtt tcaatcccac agcggctccc cctgaaaatc      9600
agagcgaggt tccagagctc cgccttaggg gttgggcttc tggcagccaa gtaccgcccc      9660
ttctacccca agatgggata taaagtctct tagctccttc cagagaagag taagaagaaa      9720
gaaaccatca caggacctct aaggaagaga ggaattgtac actcacctcc gtggcatctg      9780
tgggcattgc ttgcctgctt agctgtagcg gggggttcag cttgcatg               9828

<210> SEQ ID NO 2
<211> LENGTH: 9450
<212> TYPE: DNA
<213> ORGANISM: Artificial Sequence
<220> FEATURE:
<223> OTHER INFORMATION: Description of Artificial Sequence: 9.5 kb
      region of the EPX gene locus

<400> SEQUENCE: 2
ttctcagatg gtatgatttg acacagagct gggattatct ctgaaaggtt gtggggtgac       60
tttatgtatt aggctaaaca ccactccatg actctcagca gatgccaaat accttttaaat     120 tttgattttg tcactcagtg tggtggtcag atatgtttga aggcttcgtg gaaattagca      180
aaggttccgc ctctatggga ctgatgtaac tcagagaaac cagagaatac cacccggaga      240
gcaaaatgca ggctggcttg caatccccac atcctctcct gattaaactg ttaactttac      300
```

-continued

```
actctgactc tgacattcat gattttatgt gttttgagtt gctaacatgc aaaaatgcac    360
aactgtgggc cttttcttc tttctattt tattttatta tttttattat ttaattaatt    420
ttttacactc catattttat tcccccatc caccctccaa ctgttccaca tcccatacct    480
cctcccacc ccctgtctc catgtggatg tccccacccc cgtcccacct gacctctaaa    540
ctccctgggg cctccagtct cttaagggtt aggtgcatca tctctgaatg aacacagacc    600
tgaaagtcct ctactgtatg tgtgttgggg gcctcatatc agctagtgta ccctgcctgt    660
ttgatggtct aatgtttgcg agatctcggg gtccagatta attgagactg ctggtgctcc    720
tataggatca cccttctcct cagcttcttt cagccttccc taattcaacc acagggtca    780
gctgcttctg tccactggtt gggtgcaaat atctgcatct gattctttca gctgcttgtt    840
gggtcttcca gagtgtggtc atgacaggtc ccttttgta agctctccat agcctcagtg    900
atagagtcag gccttggaac cttcccttga gctggatctc actttgggcc tgtcgctgga    960
ccttcttttc ctcaatatcc tctccatttc catccctgta attctttcag acaggaacaa    1020
ttatgggtca gagatgtgac tgtgggatgg caaccccatc cctcacttga tatcctgtct    1080
tcctgctgga ggtgggctct gtaatttccc tcttctactg tcctgcagtt catctaaggt    1140
cccttccttt gagtcccgag agtctctcac ctcccaggtt tctggtgctt tatggagggt    1200
ccccccaacc ttctatctcc tgaggttgcc tgtttccatt cttctgctg ccccttaggg    1260
cttcagtcct tttccctcac ccaataccag atcaggttcc ccttcttccc ccctccccc    1320
ccccggggg gggcttttc ttatagagga actgtgttgg ttgtatgtgt gcactggaat    1380
gtatgagtat gcatgtgtgt gtgtgtgtgt gtgcatatgt atggaggcca gatgtcaacc    1440
ctggacattt ttttcttaga catggtcaat cttgctttaa atctttttt tttttaatta    1500
tttttaaatt gcgaatctat ttgtgcatgt gtgtgcagta cctattaagg ccagtagagg    1560
gctcaagagc tcccggagtt ggagttacag gcggttgtga attgccttag gagcttagga    1620
tgcttagaag ctctctctct ttgttttga gacaagacaa gcgctttcat taggacttgg    1680
gacttgttga ttaggttcag tggccattgt acctcagggg tactccagcc tctccctccc    1740
caacacaggg gtgctgcctc gcctggctta aaaaaaaat taaaattaaa aaaaaatgt    1800
gggccgggca atagtggcac acactttaa tctcagcact tgggagacag aggcaggcag    1860
atctccaagt tccaggacag ccagagcagc taggcatggt gggacacatt ttcaatccca    1920
ccactgatga agcagaggta gatttctgta agttctatgt ggtaagttct gggacagcca    1980
gggattttt tttttttttt agtgagtgcc tgcacacatg catgtgcatc gtgtgtgtct    2040
ggtacccaca gagggcatca gattgcctgg agttagcatt acaggtgttt ctgtgcttcc    2100
taactctgac tttggctttg tgtgtgagca gcaagtgctc ttagcttagg agccctctat    2160
ccagacctcc atgtctggtt tctcaggtgg tttccaggga tagaacttgg gtcctcctgt    2220
tcaagcagca agctctccct caccctatgc tggtccttta ttgaatacaa gtgagcccag    2280
gggacctgag gaggacgcag gcttccctgt cagattccca tcaaccccta ctctgggggc    2340
cttctttctc cacaagctca acagtcagcc tagcaatcct catccaggag gctgtatagg    2400
gaattcgtct ctccagacca gctgcagagt taggactgac ccttcctgcc ttttgctgac    2460
ttgattagca gttcagagag atcaagttct tgctcaaagc cacacaggtg ggtcaagcca    2520
tgacagaagt gggagtagtg ctggacttcc agccagctct ccagagcccc aagctgcact    2580
gtcagacttg gtgagtaaag gcaaggaact cagagctgtc ttttcagaac aacacacaca    2640
```

```
cacacacaca cacacacaca cacacacaca cacacacaca gagagagaga gagagagaga    2700
gagagagaga tgcagacaga tacacatata cagacacaca gacacataca tagacacata    2760
cacagttgca gacagacaca caaacagaca tatacagaca cacatataca gacacataca    2820
tagtcaaaca cacacccaga tgcagacaca cagacacata caaacacaca cacacacaga    2880
cacagaaact cagagacaca tacaaacaca cacacagata cacacagaaa cacagtcaca    2940
gacatacagg cacacagaga gacacacaca gaaacacaca gtgacacact cacacacaga    3000
cacaccatca tacacacaca gtggtgcaca cagacacatg cacacacagt gacacacaca    3060
gagagacaca cacacatcag cctctggcac agtgtgctgc cactaaggtt taggcaagct    3120
ccctttccat gcacatctca gtgttctcaa agttacacca ggacaaatga cccccttttcc    3180 aaagaaaccc tgggagcaag ggtgggtctg ccaagcctga gccttgctgt gtccctgtc     3240 ttaatgggc  agttggagca gagcagataa agagatccga tcaggcctgt ggccagcagt    3300
tccaccatgg cgggtagaca gttcttgtga aagtgattgc agaaggatga ggtttcagac    3360
tgcccaggga ggaggggagg ggaggtcctc cagtgctgcc gattaagagt cctgagaaag    3420
aagctgtcct catggtccat ggcctggtct gccacagcat ccagtgaccc acagcaaggc    3480
tggtccaggg atggccctta ccataggtac tgggtcctga catgcacggg cacaaatcca    3540
tctcctgacc caacagcaat ggcaggcaag gtcacagcaa acacatctgc tccacaaatc    3600
ctaccaggcc tgccaggcac acctaggtag gaggctactg tgggcaaacg ccttttctgt    3660
gcggaacttg aggagcgtat tggattcata agcacatgat gaattttgga aagaaactgt    3720
gagactaaga accagagggc ctaagcctgc cgagtcttgg aaggattccc tgtggatgag    3780
tgagacctag gaactcagtg ggagtcagcc aggcggagac aaagagcctt cagggcttgc    3840
gacttgtgtc tgtctgaaag atggtagact ttgctatgaa gctgaaagcc agtgtgctta    3900
ggaagcagag gaataggttt accctgcagg tgaggcagga gccagggttc tgagatggag    3960
ggagggaagc aggcagccca agcaagcaac tgaggagctg aatggtcagg gctccacatc    4020
ccaagcactc ctagaagcct tgtcaccccca aaataataat ctcttcctca ccccctttcct   4080 cctctttctc ctcagtgctg ggcatggaac gcagccttga gaatcgtccc agccctaagt    4140
acggtccccc tcacaggtcc tgagtggccc tgcctcattg tttttatttt ggccatttcc    4200
ctataggagg aagggcttgc ctgtgagatc cccaagccta tggccttgtc attgctggaa    4260
ggaaatgtat ctaccccaga agcaggttct gggttccact tgctgaggga agagctctca    4320
tatcagcctc atagacaggc agcttcccta acacccaacc aggaggatat accctggct    4380 cctacttagt ggtctgcgca ccctctcttt tctctgctgg ttcaggctct gccctccacc    4440
ctggatctgt agcctaactg gccctggag aaggaagaga actggagaaa tcccaactag     4500
gtcagggagg ggatttgttt tttcttgcta gggtggactt agtgggttaa gcaagaaagc    4560
tactcgctct cttctgagac ctggcccag gcctctgctg agtgttgact acacaccata     4620
gagatcaagt acggagcctc ttctcccacg cattcagaag accaatggac gtggtgacgt    4680
cattccttcg ttaaagttca atatgtgctg agaaacatca gtgctgagaa acatcactgt    4740
ggggtgcccc atagatcaaa gagggacatc agagatgtct ttggaggcga gcagaaagtg    4800 gccaacgaa  ggccttctgg ctgaggttag ggtaaaatga gtggagttat tctggcaaca    4860
aggactgcgg atggatctag aagtggggga agggcacatc cattaaggct ggggtgtggt    4920
ggatggtggg gaggaacgat agtggaggct agggagaagc tgtgagcctg aggggtgtg     4980 gaagcattgg ggctcctgct gctcaataga ccaggtcact gtgcacccag cccttcccct    5040
```

```
ccctgggtgc tcagaaccca gtgattccct cctcactcaa aatacatgga ccggtgggtt    5100
gtggagggag tagaaagcct cctgttttgt cgctaatgaa ggagcaaagc gagctgttca    5160
cccttgcaca aaagctaagg ggttccgtga accccttgga gtcattaccc cagggaatca    5220
ttaaacaagg tcaggtggct cttgaggtcc actctgccgt tgttactcta aacaatcgca    5280
gcaataaaat tctcctcccc aagtacagtt tgtgccgctc tatatgctaa gtgattgctg    5340
ccaatactgt ttaactttaa taaccccgt gagttcaagt cagtgggttt tttttttta     5400 ttgcgcataa gaaccgtggt taatttagga agttcccagt tatacaatgg ctgcctctgc    5460
tgtgtgcgtt tacttcaaga gtaaggacaa agctgtgcac gattgtattt acacatttca    5520
cttgcctggg gatgtatctc tgctgaaaga gtgcttcctt agcatacaca aggtcctggc    5580
aatccctggc accacatgaa ctgggggtgt gggtggggtg gaatatgcct gtaaccccag    5640
cactgggtag gagtgattag gagaagccaa agttcaaggt catctttggc tacatagcaa    5700
gtttgaagct agcctagact acgtgaaacc ctgtctcaaa caaaacaaaa aatagttgat    5760
ataaatgata gcacagtact tataaagttg aaagaaatag aatctgattt ccttttaatt    5820
ctgttgttct acgtgaaggc tggcatttta attaatataa gattcaagtt taaaacagtg    5880
tgtgaaaact gtatctttta aaagatata ttttattaa gttttaactt cttgtagata     5940
tacacatatc tgtgtgtagg tgtgtgcata caggcgccct gggaatccag agaagggcat    6000
tggatcccct ggagctggag ttacaggcct ggaagctgtt gaatgtaggt gctgggaaca    6060
gaacccgggt cctctggaag tgctctaagc cactgagcca tctccccagc cctgaaaca    6120 gtatcttcct gtacaactga cttcacatgt gaaatggttt tacgggtttt ttatgccttc    6180
aagattgagc tgtttcttct ctttaaacgc ccgtttgtct gttttgga tgccctgct     6240 gcgtagctca gggcgatctc taactgcatc agtctcccac gtgttgggat ggcagcggtg    6300
tgccgccgca cctggtggaa ctgctgactc taaaactaaa gaagaaattt agtacttaac    6360
tatattttga atactaaagc tgctaatata agccaggtgt gtgtgttatc acacatctgt    6420
aattttggcc cttgggaggg ggaaggagga ggaagagttt caagccagcc aggacttcat    6480
gaggttctgt tccaaacacc taaaccaacc aaccaccacc accaccacca caaaaatct    6540 aacaatatgt ggatatttcc ccttaagtta aaaacattaa gccattacat ttttcctttt    6600
atatagttag tatgtttgca tgcatgcatg tatttgttta tttccagagt ctcatgcatt    6660
ttagactgat ctctaacttc ctgtgtagct gtggcagacc ttgaacttca atctttcagc    6720
taatatatat tatgtattat atatatatgt atgtatgtat atatatatat ataatacata    6780
atatacacac atacatacat acacaatata tatatacaca cacatttata tatacacaca    6840
tacatacaca atatatatac atatacatat atatatacac atacacacat atacatatat    6900
attttactga cacaattata tacattaaga tcaataaaag aaaacctcct cacatttctg    6960
gccattacta tttgtttcat ttaatgagta tctttcaaaa ttattttaat gggtagagga    7020
ggatactgaa ggaggcccta gtgtctgaca cacttcgttg ctactggaca aaacttagct    7080
acaaggaaaa tctctcctat gagttgctga gagaaaagac tcatgggaaa gcctgagaac    7140
ccatagtctt tgcccacact cctccccctgg tccctctgat cacgacaact aagaagaaag    7200
tcaatgtcag agctgactac catgagcatg tgcggaccct gcctgtctgt cagacctgtc    7260
acagtgaagg ccacagtggg tgcctaggct ggagggcacc tcaccttgtc cagggctcca    7320
tcttcatcag gtccctgtgg cctcagcccc agaactaggt gccaatgcct tcattttaga    7380
```

-continued

```
ggcctcccct ttagaaatct agccctgaag gatccaaaga cgcttttgca ttcttcgctc    7440
ctgcctccca gctgaagcca atggctgcct gaggggacag ccccgtgtaa agtaacaaa    7500 gaagcaacaa taagatagaa caatgaggct tcttcagtgc cctgcttgcc aggcactgtg    7560
gtggtgtgtc acatgttcta ccaggagcta gggaaacctc cactgtgcag gagaaggcct    7620
ttaggcccag cacttgcctc acaggatgat gggattgtat caggagctct tgaggacttc    7680
tttgagctgc tctcaggggg ctccttggtg ctgagtacag gatttaggtc ccagcttgat    7740 ttgagaggg gtcagacgtg gcatcctaga gggagctagg caaaggggat ggcattcatc    7800
aaagggagag gatcataaac agaagattag catggttggt gctctggaca gggtcccgta    7860
ggagagcagc tgagtgtaag gtgaagggag cacgtggccc caggggttag aagagccatg    7920
tgacaagcca tacttcttca gtctcctgaa tgagctttac ccactagtcc agacccaaga    7980
ggcagcttaa gcaacatccc cagaacttgc cttccacagt cagggtctgt agggtccctc    8040
aggctctcag tcaaatcttt aagcctaact tgttaagata cccaaatata acaaatgtag    8100
caggtaggga tggatctaga gcccagtgct ctgcccctgg ttcatccccc aaactcactg    8160
cattccatcg ctaggaccac tctcaactaa ctggctgctg ttaaagaact aatgaccct    8220 ttaggggaga gcagagttct gtgggggtat ggcgtccctg gaaggagggc atcctagctc    8280
tagcctgggg catctggagg ggaggggaaag ctcagctgtg catggtaccg tttaaaatct    8340
cttgggatca ccattctggc tcttaagctt ggaaacggag gtctagcagg gtatgtcggg    8400
agatctagtc gaccttcatc cttccttgta attttgtatc ccttggcaaa caggttcggc    8460
ctctgctgaa gatgggagat aagataggg aagccttgcc aacaggagct tgtgaaagga    8520
gttgctaaag caaaatggct gtttcaggag caactgttga ggccggtggc agaggaggga    8580
gcactgatga gggaggagga agcactgatg cgggaggagg ggcaggggaa ggcgttgtgc    8640
aggttgaggt gggacagggg ttgaagagcc cggggaaagag tctcctgagg tctaggaagg    8700
aatggacatg ctcacctgaa gggaccagga taggttggtt accagcacag tggcagtggc    8760
tttggagcca gagaccaaca ctagccatca aggcaggcaa ggatcaacag gctcctccag    8820
agaagggcct gtcagaagga aaggcttgaa agtgtgaagg aaggagctgc ggcccgactg    8880
agttgagttc tgcccaagat ctcactgcct gtgaaagagc cagatggaga ctcaggtcag    8940
tcaggcctag tgcagcaatc tctttcacgg gagcacacag taagcccacc actgctgtgc    9000
attgagagga gatcagggca cgctcagagc cacagtgagc ctttaggtct gggcaggaag    9060
cttccagcag ttcactcgct gtgagttcta cctgtgacac ctcaccatga ccccaggtgt    9120
cccctgaggt atttctctgg catcttggag ggagcagatc gccctaggga gataaggaga    9180
gaactggatt attgacgact cactcctcta caaacattta atgaacgcct actgaatgga    9240
gccttgtgct gagtattagg ggtatggtaa tatgtctgga ccccctttct gccctgatgg    9300
ggagagagga acctttccaa acatccacac aaaacctatt ttagggatgt gaaaatgagt    9360
gacaattagc gatggggcca agctctctct ttttgtcagt aacgaggtca ttcatcactc    9420
attgggtgac acctccatcc ccagcactgc                                    9450
```

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: primer
      lucF1

```
<400> SEQUENCE: 3
gccattctat ccgctggaag atgg                                          24

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: primer
      lucR4

<400> SEQUENCE: 4
cgattttacc acatttgtag aggttttact tgc                                33

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: PCR
      primer 1

<400> SEQUENCE: 5
agtcaagctt cagggtgagt ctatgggacc cttg                               34

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: PCR
      primer 2

<400> SEQUENCE: 6
gactaagctt aggagctgtg ggaggaagat aagag                              35

<210> SEQ ID NO 7
<211> LENGTH: 9757
<212> TYPE: DNA
<213> ORGANISM: Artificial Sequence
<220> FEATURE:
<223> OTHER INFORMATION: Description of Artificial Sequence: 9.8 kb
      restriction fragment

<400> SEQUENCE: 7
ttctcagatg gtatgatttg acacagagct gggattatct ctgaaaggtt gtggggtgac    60
tttatgtatt aggctaaaca ccactccatg actctcagca gatgccaaat acctttaaat   120
tttgattttg tcactcagtg tggtggtcag atatgtttga aggcttcgtg gaaattagca   180
aaggttccgc ctctatggga ctgatgtaac tcagagaaac cagagaatac cacccggaga   240
gcaaaatgca ggctggcttg caatccccac atcctctcct gattaaactg ttaactttac   300
actctgactc tgacattcat gattttatgt gttttgagtt gctaacatgc aaaaatgcac   360
aactgtgggc cttttctctc ttttctattt tattttatta tttttattat ttaattaatt   420
ttttacactc catattttat tccccccatc caccctccaa ctgttccaca tcccatacct   480
cctccccacc cccctgtctc catgtggatg tccccacccc cgtcccacct gacctctaaa   540
ctccctgggg cctccagtct cttaagggtt aggtgcatca tctctgaatg aacacagacc   600
tgaaagtcct ctactgtatg tgtgttgggg gcctcatatc agctagtgta ccctgcctgt   660
ttgatggtct aatgtttgcg agatctcggg gtccagatta attgagactg ctggtgctcc   720
tataggatca cccttctcct cagcttcttt cagccttccc taattcaacc acaggggtca   780
```

```
gctgcttctg tccactggtt gggtgcaaat atctgcatct gattctttca gctgcttgtt    840
gggtcttcca gagtgtggtc atgacaggtc cctttttgta agctctccat agcctcagtg    900
atagagtcag gccttggaac cttcccttga gctggatctc actttgggcc tgtcgctgga    960
ccttcttttc ctcaatatcc tctccatttc catccctgta attctttcag acaggaacaa   1020
ttatgggtca gagatgtgac tgtgggatgg caacccatc cctcacttga tatcctgtct     1080
tcctgctgga ggtgggctct gtaatttccc tcttctactg tcctgcagtt catctaaggt   1140
cccttccttt gagtcccgag agtctctcac ctcccaggtt tctggtgctt tatggagggt   1200 cccccccaacc ttctatctcc tgaggttgcc tgtttccatt ctttctgctg cccttaggg    1260 cttcagtcct tttccctcac ccaataccag atcaggttcc ccttcttccc cctccccccc   1320
ccccgggggg gggcttttc ttatagagga actgtgttgg ttgtatgtgt gcactggaat     1380
gtatgagtat gcatgtgtgt gtgtgtgtgt gtgcatatgt atggaggcca gatgtcaacc   1440
ctggacattt ttttcttaga catggtcaat cttgctttaa atctttttt tttttaatta    1500 tttttaaatt gcgaatctat ttgtgcatgt gtgtgcagta cctattaagg ccagtagagg   1560
gctcaagagc tcccggagtt ggagttacag gcggttgtga attgccttag gagcttagga   1620
tgcttagaag ctctctctct ttgttttga dacaagacaa gcgctttcat taggacttgg    1680
gacttgttga ttaggttcag tggccattgt acctcagggg tactccagcc tctccctccc   1740
caacacaggt gtgctgcctc gcctggctta aaaaaaaat taaaattaaa aaaaaatgt     1800 gggccgggca atagtggcac acacttttaa tctcagcact gggagacag aggcaggcag    1860 atctccaagt tccaggacag ccagagcagc taggcatggt gggacacatt ttcaatccca   1920
ccactgatga agcagaggta gatttctgta agttctatgt ggtaagttct gggacagcca   1980 gggattttt tttttttttt agtgagtgcc tgcacacatg catgtgcatc gtgtgtgtct    2040
ggtacccaca gagggcatca gattgcctgg agttagcatt acaggtgttt ctgtgcttcc   2100
taactctgac tttggctttg tgtgtgagca gcaagtgctc ttagcttagg agccctctat   2160
ccagacctcc atgtctggtt tctcaggtgg tttccaggga tagaacttgg gtcctcctgt   2220
tcaagcagca agctctccct caccctatgc tggtccttta ttgaatacaa gtgagcccag   2280
gggacctgag gaggacgcag gcttccctgt cagattccca tcaaccccta ctctgggggc   2340
cttctttctc cacaagctca acagtcagcc tagcaatcct catccaggag gctgtatagg   2400
gaattcgtct ctccagacca gctgcagagt taggactgac ccttcctgcc ttttgctgac   2460
ttgattagca gttcagagag atcaagttct tgctcaaagc cacacaggtg ggtcaagcca   2520
tgacagaagt gggagtagtg ctggacttcc agccagctct ccagagcccc aagctgcact   2580
gtcagacttg gtgagtaaag gcaaggaact cagagctgtc ttttcagaac aacacacaca   2640
cacacacaca cacacacaca cacacacaca cacacacaca gagagagaga gagagagaga   2700
gagagagaga tgcagacaga tacacatata cagacacaca gacacataca tagacacata   2760
cacagttgca gacagacaca caaacagaca tatcagaca cacatataca gacacataca    2820
tagtcaaaca cacacccaga tgcagacaca cagacacata caaacacaca cacacacaga   2880
cacagaaact cagagacaca tacaaacaca cacagataca cacagaaa cacagtcaca     2940 gacatacagg cacacagaga gacacacaca gaaacacaca gtgacacact cacacacaga   3000
cacaccatca tacacacaca gtggtgcaca cagacacatg cacacacagt gacacacaca   3060
gagagacaca cacacatcag cctctggcac agtgtgctgc cactaaggtt taggcaagct   3120
```

| | |
|---|---|
| cccctttccat gcacatctca gtgttctcaa agttacacca ggacaaatga ccccctttcc | 3180 |
| aaagaaaccc tgggagcaag ggtgggtctg ccaagcctga gccttgctgt gtccctgtc | 3240 |
| ttaatgggc agttggagca gagcagataa agagatccga tcaggcctgt ggccagcagt | 3300 |
| tccaccatgg cgggtagaca gttcttgtga aagtgattgc agaaggatga ggtttcagac | 3360 |
| tgcccaggga ggaggggagg ggaggtcctc cagtgctgcc gattaagagt cctgagaaag | 3420 |
| aagctgtcct catggtccat ggcctggtct gccacagcat ccagtgaccc acagcaaggc | 3480 |
| tggtccaggg atggcccta ccataggtac tgggtcctga catgcacggg cacaaatcca | 3540 |
| tctcctgacc caacagcaat ggcaggcaag gtcacagcaa acacatctgc tccacaaatc | 3600 |
| ctaccaggcc tgccaggcac acctaggtag gaggctactg tgggcaaacg ccttttctgt | 3660 |
| gcggaacttg aggagcgtat tggattcata agcacatgat gaattttgga aagaaactgt | 3720 |
| gagactaaga accagagggc ctaagcctgc cgagtcttgg aaggattccc tgtggatgag | 3780 |
| tgagacctag gaactcagtg ggagtcagcc aggcggagac aaagagcctt cagggcttgc | 3840 |
| gacttgtgtc tgtctgaaag atggtagact ttgctatgaa gctgaaagcc agtgtgctta | 3900 |
| ggaagcagag gaataggttt accctgcagg tgaggcagga gccagggttc tgagatggag | 3960 |
| ggagggaagc aggcagccca agcaagcaac tgaggagctg aatggtcagg gctccacatc | 4020 |
| ccaagcactc ctagaagcct tgtcacccca aaataataat ctcttcctca ccccttcct | 4080 |
| cctctttctc ctcagtgctg ggcatggaac gcagccttga gaatcgtccc agccctaagt | 4140 |
| acggtccccc tcacaggtcc tgagtggccc tgcctcattg ttttattt ggccatttcc | 4200 |
| ctataggagg aagggcttgc ctgtgagatc cccaagccta tggccttgtc attgctggaa | 4260 |
| ggaaatgtat ctaccccaga agcaggttct gggttccact tgctgaggga agagctctca | 4320 |
| tatcagcctc atagacaggc agcttcccta acacccaacc aggaggatat acccctggct | 4380 |
| cctacttagt ggtctgcgca ccctctcttt tctctgctgg ttcaggctct gcctccacc | 4440 |
| ctggatctgt agcctaactg gcccctggag aaggaagaga actggagaaa tcccaactag | 4500 |
| gtcaggagg ggatttgttt tttcttgcta gggtggactt agtgggttaa gcaagaaagc | 4560 |
| tactcgctct cttctgagac ctggccccag gcctctgctg agtgttgact acacaccata | 4620 |
| gagatcaagt acgagcctc ttctcccacg cattcagaag accaatggac gtggtgacgt | 4680 |
| cattccttcg ttaaagttca atatgtgctg agaaacatca gtgctgagaa acatcactgt | 4740 |
| ggggtgcccc atagatcaaa gagggacatc agagatgtct ttggaggcga gcagaaagtg | 4800 |
| gccaacggaa ggccttctgg ctgaggttag ggtaaaatga gtggagttat tctggcaaca | 4860 |
| aggactgcgg atggatctag aagtggggga agggcacatc cattaaggct ggggtgtggt | 4920 |
| ggatggtggg gaggaacgat agtggaggct agggagaagc tgtgagcctg aggggtgtg | 4980 |
| gaagcattgg ggctcctgct gctcaataga ccaggtcact gtgcacccag cccttcccct | 5040 |
| ccctgggtgc tcagaaccca gtgattccct cctcactcaa aatacatgga ccggtgggtt | 5100 |
| gtggagggag tagaaagcct cctgttttgt cgctaatgaa ggagcaaagc gagctgttca | 5160 |
| cccttgcaca aaagctaagg ggttccgtga acccttgga gtcattaccc cagggaatca | 5220 |
| ttaaacaagg tcaggtggct cttgaggtcc actctgccgt tgttactcta aacaatcgca | 5280 |
| gcaataaaat tctcctcccc aagtacagtt tgtgccgctc tatatgctaa gtgattgctg | 5340 |
| ccaatactgt ttaactttaa taaccccgt gagttcaagt cagtgggttt ttttttta | 5400 |
| ttgcgcataa gaaccgtggt taatttagga agttccagt tatacaatgg ctgcctctgc | 5460 |
| tgtgtgcgtt tacttcaaga gtaaggacaa agctgtgcac gattgtattt acacatttca | 5520 |

```
cttgcctggg gatgtatctc tgctgaaaga gtgcttcctt agcatacaca aggtcctggc      5580
aatccctggc accacatgaa ctgggggtgt gggtggggtg gaatatgcct gtaaccccag      5640
cactgggtag gagtgattag gagaagccaa agttcaaggt catctttggc tacatagcaa      5700
gtttgaagct agcctagact acgtgaaacc ctgtctcaaa caaacaaaa aatagttgat       5760 ataaatgata gcacagtact tataaagttg aaagaaatag aatctgattt cctttttaatt    5820 ctgttgttct acgtgaaggc tggcatttta attaatataa gattcaagtt taaaacagtg     5880
tgtgaaaact gtatctttta aaagatata tttttattaa gttttaactt cttgtagata      5940
tacacatatc tgtgtgtagg tgtgtgcata caggcgccct gggaatccag agaagggcat    6000
tggatcccct ggagctggag ttacaggcct ggaagctgtt gaatgtaggt gctgggaaca    6060
gaacccgggt cctctggaag tgctctaagc cactgagcca tctccccagc cctggaaaca    6120
gtatcttcct gtacaactga cttcacatgt gaaatggttt tacgggtttt ttatgccttc    6180
aagattgagc tgtttcttct ctttaaacgc ccgtttgtct gttttttggga tgcccctgct   6240 gcgtagctca gggcgatctc taactgcatc agtctcccac gtgttgggat ggcagcggtg    6300
tgccgccgca cctggtggaa ctgctgactc taaaactaaa gaagaaattt agtacttaac    6360
tatattttga atactaaagc tgctaatata agccaggtgt gtgtgttatc acacatctgt    6420
aattttggcc cttgggaggg ggaaggagga ggaagagttt caagccagcc aggacttcat    6480
gaggttctgt tccaaacacc taaaccaacc aaccaccacc accaccacca acaaaaatct    6540
aacaatatgt ggatatttcc ccttaagtta aaaacattaa gccattacat ttttcctttt    6600
atatagttag tatgtttgca tgcatgcatg tatttgttta tttccagagt ctcatgcatt    6660
ttagactgat ctctaacttc ctgtgtagct gtggcagacc ttgaacttca atctttcagc    6720
taatatatat tatgtattat atatatatgt atgtatgtat atatatatat ataatacata    6780
atatacacac atacatacat acacaatata tatatacaca cacatttata tatacacaca    6840
tacatacaca atatatatac atatacatat atatatacac atacacacat atacatatat    6900 atttttactga cacaattata tacattaaga tcaataaaag aaaacctcct cacatttctg    6960
gccattacta tttgtttcat ttaatgagta tcttttcaaaa ttattttaat gggtagagga    7020
ggatactgaa ggaggcccta gtgtctgaca cacttcgttg ctactggaca aaacttagct    7080
acaaggaaaa tctctcctat gagttgctga gagaaaagac tcatgggaaa gcctgagaac    7140
ccatagtctt tgcccacact cctccctgg tccctctgat cacgacaact aagaagaaag     7200
tcaatgtcag agctgactac catgagcatg tgcggaccct gcctgtctgt cagacctgtc    7260
acagtgaagg ccacagtggg tgcctaggct ggagggcacc tcaccttgtc cagggctcca    7320
tcttcatcag gtccctgtgg cctcagcccc agaactaggt gccaatgcct tcattttaga    7380
ggcctccctt ttagaaatct agccctgaag gatccaaaga cgcttttgca ttcttcgctc    7440
ctgcctccca gctgaagcca atggctgcct gaggggacag ccccgtgtaa aggtaacaaa    7500
gaagcaacaa taagatagaa caatgaggct tcttcagtgc cctgcttgcc aggcactgtg    7560
gtggtgtgtc acatgttcta ccaggagcta gggaaacctc cactgtgcag gagaaggcct    7620
ttaggcccag cacttgcctc acaggatgat gggattgtat caggagctct tgaggacttc    7680
tttgagctgc tctcagggg ctccttggtg ctgagtacag gatttaggtc ccagcttgat     7740
ttgagagggg gtcagacgtg gcatcctaga gggagctagg caaaggggat ggcattcatc    7800
aaagggagag gatcataaac agaagattag catggttggt gctctggaca gggtcccgta    7860
```

```
ggagagcagc tgagtgtaag gtgaagggag cacgtggccc cagggggttag aagagccatg    7920 tgacaagcca tacttcttca gtctcctgaa tgagctttac ccactagtcc agacccaaga    7980
ggcagcttaa gcaacatccc cagaacttgc cttccacagt cagggtctgt agggtccctc    8040
aggctctcag tcaaatcttt aagcctaact tgttaagata cccaaatata acaaatgtag    8100
caggtaggga tggatctaga gcccagtgct ctgcccctgg ttcatccccc aaactcactg    8160
cattccatcg ctaggaccac tctcaactaa ctggctgctg ttaaagaact aatgacccct    8220
ttaggggaga gcagagttct gtggggtat ggcgtccctg aaggagggc atcctagctc    8280 tagcctgggg catctggagg ggaggaaag ctcagctgtg catggtaccg tttaaaatct    8340
cttgggatca ccattctggc tcttaagctt ggaaacggag gtctagcagg gtatgtcggg    8400
agatctagtc gaccttcatc cttccttgta attttgtatc ccttggcaaa caggttcggc    8460
ctctgctgaa gatgggagat aagataggg aagccttgcc aacaggagct tgtgaaagga    8520
gttgctaaag caaatggct gtttcaggag caactgttga ggccggtggc agaggaggga    8580
gcactgatga gggaggagga agcactgatg cgggaggagg ggcaggggaa ggcgttgtgc    8640
aggttgaggt gggacagggg ttgaagagcc ggggaagag tctcctgagg tctaggaagg    8700
aatggacatg ctcacctgaa gggaccagga taggttggtt accagcacag tggcagtggc    8760
tttggagcca gagaccaaca ctagccatca aggcaggcaa ggatcaacag gctcctccag    8820
agaagggcct gtcagaagga aaggcttgaa agtgtgaagg aaggagctgc ggcccgactg    8880
agttgagttc tgcccaagat ctcactgcct gtgaaagagc cagatggaga ctcaggtcag    8940
tcaggcctag tgcagcaatc tctttcacgg gagcacacag taagcccacc actgctgtgc    9000
attgagagga gatcagggca cgctcagagc cacagtgagc ctttaggtct gggcaggaag    9060
cttccagcag ttcactcgct gtgagttcta cctgtgacac ctcaccatga ccccaggtgt    9120
cccctgaggt atttctctgg catcttggag ggagcagatc gccctaggga gataaggaga    9180
gaactggatt attgacgact cactcctcta caaacattta atgaacgcct actgaatgga    9240
gccttgtgct gagtattagg ggtatggtaa tatgtctgga cccccttcct gccctgatgg    9300
ggagagagga acctttccaa acatccacac aaaacctatt ttagggatgt gaaaatgagt    9360
gacaattagc gatggggcca agctctctct ttttgtcagt aacgaggtca ttcatcactc    9420
attgggtgac acctccatcc ccagcactgc ttcgggttgt gggggggcaaa tgcatccatg    9480 aacccaagac tagaggtggg tgtggaacaa ggtaatggtg gctaggggag cccccattct    9540
ggtgagttgg taaagtatga tgggggtgtt tcaatcccac agcggctccc cctgaaaatc    9600
agagcgaggt tccagagctc cgccttaggg gttgggcttc tggcagccaa gtaccgcccc    9660
ttctacccca agatgggata taaagtctct tagctccttc cagagaagag taagaagaaa    9720
gaaaccatca caggacctct aaggaagaga ggaattg                             9757
```

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Luc 3 primer

<400> SEQUENCE: 8

```
gaaatgtccg ttcggttggc agaagc                                          26
```

<210> SEQ ID NO 9
<211> LENGTH: 27

-continued

```
<212> TYPE: DNA
<213> ORGANISM: Artificial Sequence
<220> FEATURE:
<223> OTHER INFORMATION: Description of Artificial Sequence: Luc 4 primer

<400> SEQUENCE: 9
ccaaaaccgt gatggaatgg aacaaca                                          27

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: mouse EPX
      promoter primer 1

<400> SEQUENCE: 10
tgcatccatg aacccaagac taga                                             24

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: mouse EPX
      promoter primer 2

<400> SEQUENCE: 11
cccactacag ctaagcaggc aagca                                            25
```